(12) United States Patent
Togliatti

(10) Patent No.: US 11,833,075 B2
(45) Date of Patent: Dec. 5, 2023

(54) DENTAL APPLIANCE

(71) Applicant: Dante Togliatti, San Diego, CA (US)

(72) Inventor: Dante Togliatti, San Diego, CA (US)

( * ) Notice: Subject to any disclaimer, the term of this patent is extended or adjusted under 35 U.S.C. 154(b) by 209 days.

(21) Appl. No.: 15/968,045

(22) Filed: May 1, 2018

(65) Prior Publication Data

US 2018/0243124 A1 Aug. 30, 2018

Related U.S. Application Data

(63) Continuation-in-part of application No. 14/523,115, filed on Oct. 24, 2014, now Pat. No. 9,956,111.

(60) Provisional application No. 61/895,009, filed on Oct. 24, 2013.

(51) Int. Cl.
*A61F 5/56* (2006.01)
*A61C 5/90* (2017.01)

(52) U.S. Cl.
CPC ............... *A61F 5/566* (2013.01); *A61C 5/90* (2017.02)

(58) Field of Classification Search
CPC .......... A61F 5/56; A61F 5/566; A61F 71/085; A61C 5/90
USPC ........................................ 128/848, 859–861
See application file for complete search history.

(56) References Cited

U.S. PATENT DOCUMENTS

| | | | |
|---|---|---|---|
| 4,304,227 A | * | 12/1981 | Samelson ............... A61F 5/566 128/857 |
| 4,676,240 A | * | 6/1987 | Gardy ..................... A61F 5/566 128/860 |
| 5,267,862 A | | 12/1993 | Parker |
| 5,373,859 A | | 12/1994 | Forney |
| 5,465,734 A | | 11/1995 | Alvarez et al. |
| 5,499,633 A | | 3/1996 | Fenton |
| 5,562,106 A | | 10/1996 | Heeke et al. |
| 5,570,704 A | | 11/1996 | Buzzard et al. |
| 5,601,093 A | | 2/1997 | Sheehan |
| 5,810,013 A | | 9/1998 | Belfer |
| 5,816,799 A | | 10/1998 | Parker |
| 5,915,385 A | | 6/1999 | Hakimi |
| 5,921,241 A | | 7/1999 | Belfer |
| 6,244,865 B1 | | 6/2001 | Nelson et al. |
| 6,494,209 B2 | | 12/2002 | Kulick |
| 6,766,802 B1 | | 7/2004 | Keropian |

(Continued)

FOREIGN PATENT DOCUMENTS

| EP | 0599445 A1 | 6/1994 |
|---|---|---|
| EP | 0599445 B1 | 11/1998 |

(Continued)

*Primary Examiner* — Keri J Nelson
(74) *Attorney, Agent, or Firm* — Jafari Law Group, Inc.

(57) ABSTRACT

The invention is generally a dental appliance that, in exemplary embodiments, includes a mouthpiece equipped with a tongue-securing mechanism. The dental appliance helps keep a user's airway unobstructed by securing a tip portion of the tongue slightly forward relative to the mouth so that the tongue is held from falling back into the throat. This invention helps alleviate problems including severe snoring and sleep apnea, which are typically caused by the tongue obstructing the airway at the throat, thus impeding respiration during sleep or when unconscious. In an exemplary embodiment, the dental appliance comprises a mouthpiece which is configured to circumscribe a tongue retaining mechanism, or tongue sleeve, that secures a user's tongue in place.

18 Claims, 22 Drawing Sheets

(56) References Cited

U.S. PATENT DOCUMENTS

| | | | |
|---|---|---|---|
| 7,073,506 B2 * | 7/2006 | Robertson | A61F 5/56 128/848 |
| 7,533,674 B2 | 5/2009 | Dort | |
| 7,607,439 B2 | 10/2009 | Li | |
| 7,757,693 B2 | 7/2010 | Toussaint | |
| 7,861,722 B2 | 1/2011 | Keropian | |
| 7,861,724 B2 | 1/2011 | Keropian | |
| 7,946,292 B2 | 5/2011 | Dort | |
| 8,028,703 B1 | 10/2011 | Moses | |
| 8,028,705 B2 | 10/2011 | Li | |
| 3,127,769 A1 | 3/2012 | Walker | |
| 8,132,567 B2 | 3/2012 | Keropian | |
| 8,261,748 B1 | 9/2012 | Goldberg | |
| 8,302,609 B2 | 11/2012 | Martinez | |
| 8,347,890 B2 | 1/2013 | Li | |
| 8,371,309 B2 | 2/2013 | Diers | |
| 2002/0117178 A1 | 8/2002 | Dort | |
| 2002/0139375 A1 | 10/2002 | Kulick | |
| 2006/0289013 A1 | 12/2006 | Keropian | |
| 2007/0163603 A1 | 7/2007 | Sikora | |
| 2007/0292819 A1 | 12/2007 | Scarberry et al. | |
| 2009/0126742 A1 | 5/2009 | Summer | |
| 2009/0188510 A1 | 7/2009 | Palmer | |
| 2010/0326433 A1 | 12/2010 | Williams | |
| 2011/0120476 A1 | 5/2011 | Keropian | |
| 2011/0155143 A1 | 6/2011 | Shantha | |
| 2012/0017917 A1 | 1/2012 | Podmore et al. | |
| 2012/0138071 A1 | 6/2012 | Summer | |
| 2012/0160249 A1 | 6/2012 | Thomason et al. | |
| 2012/0234331 A1 | 9/2012 | Shantha | |
| 2012/0234332 A1 | 9/2012 | Shantha | |
| 2012/0247485 A1 | 10/2012 | Timmons | |
| 2012/0255561 A1 | 10/2012 | Shantha | |
| 2013/0068235 A1 | 3/2013 | Makower et al. | |
| 2013/0125902 A1 | 5/2013 | Danielian | |
| 2013/0186411 A1 | 7/2013 | Vaska et al. | |

FOREIGN PATENT DOCUMENTS

| | | |
|---|---|---|
| WO | WO2005000142 A2 | 1/2005 |
| WO | WO2009096889 A1 | 8/2009 |

\* cited by examiner

DENTAL APPLIANCE

PRIORITY AND CROSS-REFERENCE TO RELATED APPLICATIONS

The present application is a continuation-in-part of U.S. patent application Ser. No. 14/523,115 filed on Oct. 24, 2014, the disclosure of which is incorporated herein by reference in its entirety.

TECHNICAL FIELD OF THE INVENTION

The present invention relates in general to a dental appliance, and more specifically to a mouthpiece equipped with a tongue-securing mechanism, which secures a tip portion of the tongue slightly anterior to the mandible, so that the tongue is held from falling back into the throat. This invention helps alleviate problems including severe snoring and sleep apnea.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Devices that alleviate or altogether eliminate snoring and obstructive sleep apnea have long been sought after by afflicted consumers because of the deleterious effects such conditions can have on the individual. As a result, there exists a popular research field dedicated to managing these conditions.

While sleeping, the air pathways narrow as a result of muscle relaxation in the throat and tongue. For some people, this narrowing is greatly exacerbated by abnormally high relaxation of the aforementioned muscles, leading to sonorous respiration (snoring) or obstructive sleep apnea. For other people, the natural narrowing of the air pathways while sleeping is combined with one or more of a number of potential factors to produce snoring or sleep apnea including, but not limited to: a proportionally large tongue and/or tonsils as compared to the windpipe, excess fat tissue along the soft palate often a result of being overweight, or an inadequate ability to send/receive signals to/from the brain that otherwise help muscles remain sufficiently stiff throughout the night.

Obstructive sleep apnea, a more severe manifestation of the circumstances from which snoring arises, is characterized by substantial or complete blockage of the air pathways. It can result in the sleeper entering a gasping state after short to intermediate episodes of oxygen deprivation. In extreme cases, this can occur hundreds of times per night, typically unbeknownst to the sleeper. This disrupted sleep cycle can lead to severe sleep deprivation, snoring, headaches, sore throat, dry mouth, inadequate brain oxygenation, and choking in the short-term, in addition to high blood pressure, insulin resistance, and possible brain damage in the long-term.

Several apparatuses for treating snoring and sleep apnea exist. For instance, continuous positive airway pressure (CPAP) is a method and apparatus which utilizes a motor to push mildly-pressurized air through a tube connected to the user's mouth by way of a nasal and oral mask. The apparatus is used to prevent significant narrowing of the airway while sleeping. Despite improvements in the recent years to minimize noise generated by the motor, CPAP machines can still be disruptive to those near it. Moreover, the constant pressure from the motor can form uncomfortable pressure ulcers on the pharyngeal tissue and other nearby tissue. The noisy machine and mask can also be an obstacle to intimacy. More significantly, although it may be an effective treatment, CPAP compliance is extremely low (i.e., it is believed compliance is only about 20%) among people that have been prescribed CPAP machines.

The prior art illuminates a clear deficiency in existing snoring and obstructive sleep apnea devices. Therefore, there is a need in the art for a device or dental appliance that can incorporate a comfortable, naturally conforming mechanism to account for the plurality of causes and exacerbating factors of snoring and obstructive sleep apnea. The present invention overcomes the above described disadvantages of presently existing snoring and sleep apnea apparatus. It is to these ends that the present invention has been developed.

BRIEF SUMMARY OF THE INVENTION

To minimize the limitations in the prior art, and to minimize other limitations that will be apparent upon reading and understanding the present specification, the present invention provides a dental appliance that keeps the user's airway open while sleeping or otherwise unconscious. A dental appliance in accordance with the present invention may incorporate a mandibular advancement mouthpiece equipped with a tongue-receiving mechanism, or tongue sleeve, which may be situated in the gap between the upper and lower components of the mouthpiece.

Generally, a dental appliance in accordance with the present invention may be comprised of a mouthpiece that includes a tongue-receiving member, or tongue sleeve, which allows an airway to be kept open during sleep. The tongue sleeve may securely receive the user's tongue and keep the tongue in a forward configuration, thereby preventing the tongue from slipping back towards the throat and closing the airway. In various embodiments, the dental appliance or components thereof may be made with a number of different medical-grade polymers of moderate pliability (i.e., malleable enough to mold to the user's maxilla and mandible, but durable enough to hold its shape after fitting).

In an exemplary embodiment, the dental appliance may be molded to the shape of the user's mouth with steps comprising: placing a malleable mouthpiece into boiling water, removing said mouthpiece from the water shortly thereafter, and biting down on said mouthpiece whilst still hot, whereby it is useable very shortly thereafter. In another embodiment, the dental appliance may be molded to the shape of the user's mouth by having the user bite down on a mold, which subsequently requires a professional such as a dentist to construct the mouthpiece from said mold.

Typically, a dental appliance in accordance with the present invention comprises a mouthpiece and a tongue receiving member, or tongue sleeve, that may be integral with the mouthpiece. The tongue sleeve, in accordance with one embodiment of the present invention, may be generally designed to serve as a tongue-receiving member, preferably resembling an inverse or negative of the anterior-most portion of the tongue. In one embodiment, the tongue sleeve may be substantially spherical or semi-spherical in shape and include a concave cavity adapted to receive a tip portion of the user's tongue. In exemplary embodiments, the tongue sleeve is made of a flexible material, which may be squeezed by a user to create a suction force before inserting the tongue therein. This force may gently secure the user's tongue in place and prevent the tongue from falling back against the throat. The tongue sleeve may have the material makeup, by way of a non-limiting example, of a surgical or medical-grade polymer.

In one embodiment of the present invention, a dental appliance for alleviating snoring and other sleep disorders comprises: a mouthpiece; and a tongue sleeve integral with the mouthpiece, wherein the tongue sleeve includes a semi-spherical portion, comprising a concaved cavity for securely receiving a tip portion of a user's tongue.

In another embodiment of the present invention, a dental appliance for alleviating snoring and other sleep disorders comprises: a mouthpiece including a first arm, a second arm; and a tongue sleeve that connects the first arm to the second arm along a horizontal axis of the dental appliance, wherein the tongue sleeve includes a semi-spherical portion, comprising a concaved cavity for securely receiving a tip portion of a user's tongue.

In yet another embodiment of the present invention, a dental appliance for alleviating snoring and other sleep disorders comprises: a tongue sleeve including a semi-spherical portion, comprising a concaved cavity for securely receiving a tip portion of a user's tongue.

These and other advantages and features of the present invention are described herein with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted so as to provide a clear view of the various embodiments of the invention.

DETAILED DESCRIPTION OF THE INVENTION

Figure 1A:
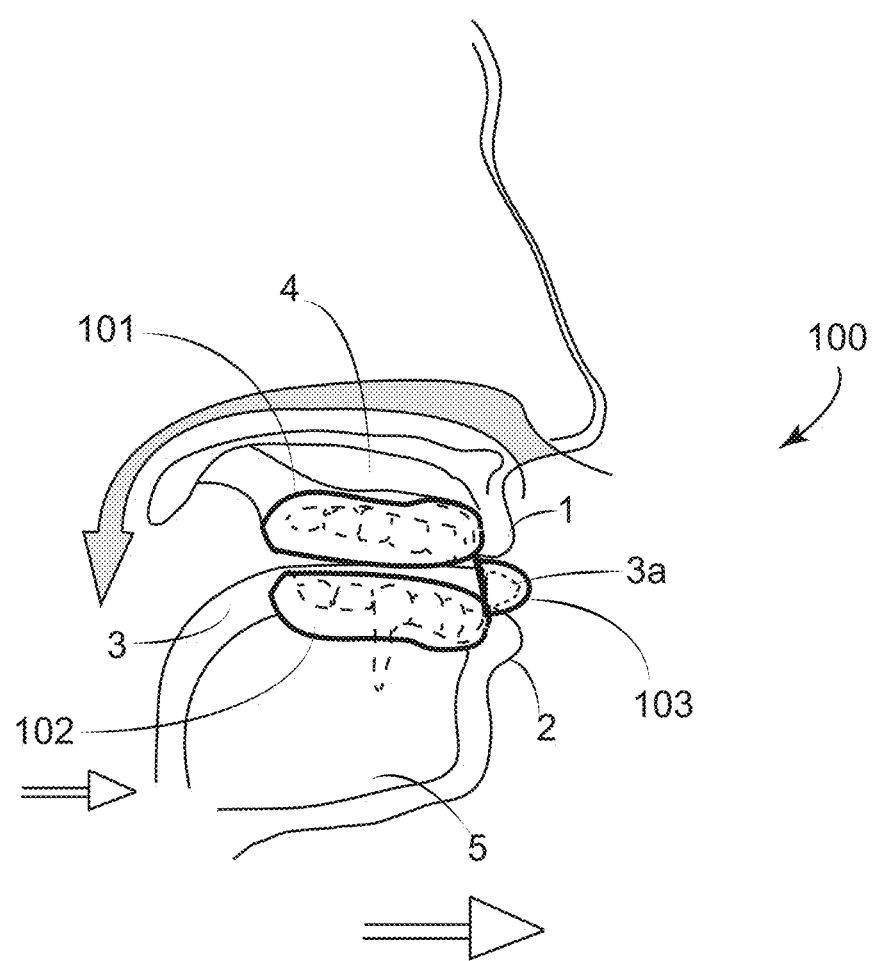
FIG. 1(a) is a schematic side view of a device, in accordance with one embodiment of the present invention, worn by a user; the separation between the maxillary and mandibular supports is exaggerated so that a tongue sleeve can more clearly be depicted.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

Turning now to the figures, FIG. 1(a) is a schematic side view of a device, in accordance with one embodiment of the present invention, worn by a user. The separation between the maxillary and mandibular components is exaggerated so that a tongue sleeve can more clearly be depicted. More specifically, FIG. 1(a) illustrates apparatus 100 being worn by a user. Unlike a CPAP machine, apparatus 100, of which a plurality of embodiments is disclosed herein, produces no audible sound since it does not require a machine or motor, and as such, does not impede restful sleep for the user or those nearby. Moreover, apparatus 100 includes tongue sleeve 103, which uniquely functions to keep the tongue of the user in a position that allows for an airway to remain open.

As pictured, the entirety of apparatus 100 fits inside a user's mouth, within the confines of upper lip 1 and lower lip 2, much like a sport's mouthpiece. The user's tongue 3 is inferiorly adjacent to maxillary component 101 of apparatus 100. Maxillary component 101 may be a stationary entity covering a plurality of the teeth of maxilla 4. Additionally, tongue 3 is superiorly adjacent to mandibular component 102 of apparatus 100. Mandibular component 102 may be a dynamic entity covering a majority of the teeth of mandible 5, which may be manipulated by the user to force lesser or greater protrusion of mandible 5 as compared to maxilla 4. A mandibular advancement mechanism, mechanism 104, which performs this manipulation is displayed and discussed with reference to FIG. 3 and FIG. 4. Together, maxillary component 101 and mandibular component 102, and optionally mechanism 104, may form a mandibular advancement mouthpiece. The material from which such mandibular advancement mouthpiece may be constructed is not to be limited. For example, and without limitation, it may comprise of a number of types of polymers, copolymers, or plastics, often thermoplastics, as well as harder materials such as gold or acrylic, or alloys composed of such materials as cobalt or chrome. Alternatives to the enumerated materials should be apparent to those skilled in the art.

Connected to the mouthpiece—maxillary component 101 and mandibular component 102—is tongue sleeve 103. Tongue sleeve 103 receives tongue 3 and securely holds the tongue in a forward configuration between maxillary component 101 and mandibular component 102, in the gap formed by their separation. Tongue sleeve 103 serves as a tongue-receiving member or the component that securely receives a tip portion of the user's tongue or tongue tip 3a. Tongue sleeve 103 may comprise multiple components or a single component without deviating from the scope of the present invention. For example, tongue sleeve 103 may be a clamping device, a suction device, or any general retaining device. In one embodiment, the tongue sleeve 103 comprises a flexible, substantially spherical or semi-spherical protrusion including an inner surface comprising a concaved portion suitable for receiving a tip portion of a user's tongue. In such an embodiment, tongue sleeve 103 may implement suction to secure the tongue. Hence, as illustrated by FIG. 1(a), a portion of tongue sleeve 103 may be configured to receive the anterior-most portion of tongue 3, or tongue tip 3a.

It should be noted that FIG. 1(a) displays a slightly exaggerated separation between maxillary component 101 and mandibular component 102 to better illustrate tongue sleeve 103. Typically, this separation is less pronounced and thus provides a snugger fit in the user's mouth.

Figure 1B:
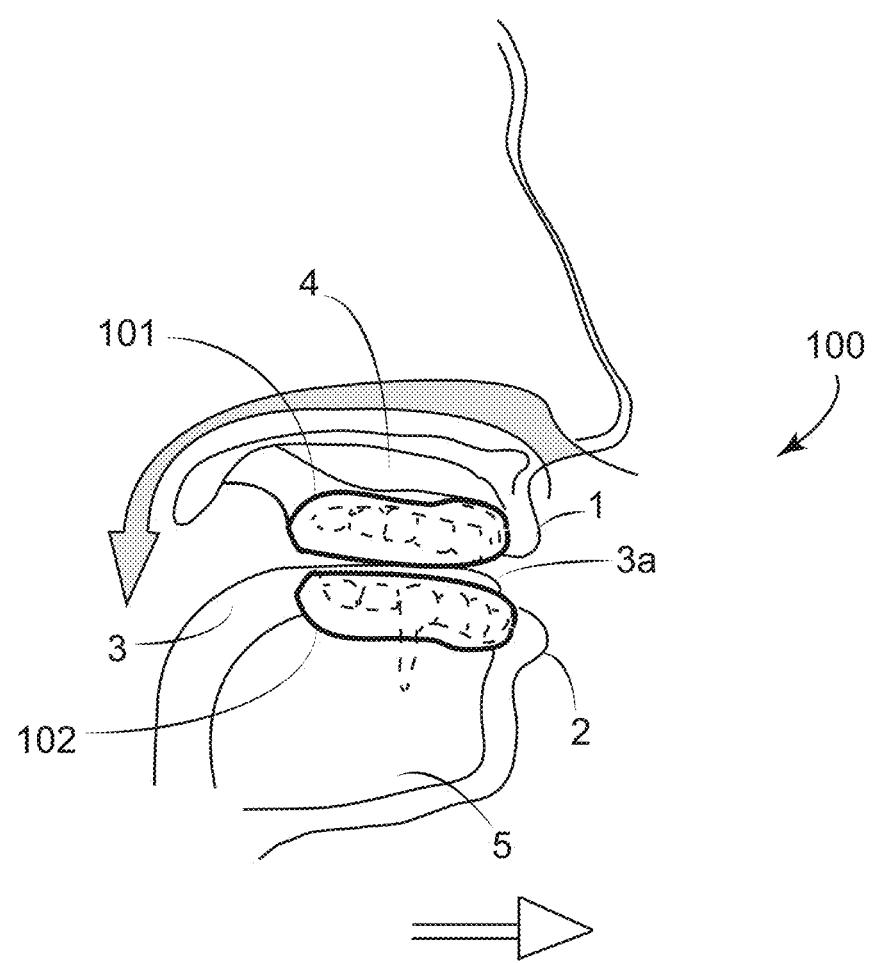
FIG. 1(b) is a schematic side view of the device illustrated in FIG. 1(a), absent the tongue sleeve, in accordance with one embodiment of the present invention, wherein the tongue sleeve may be removably attached to the mouthpiece.

As shown in FIG. 1(a) and FIG. 1(b), the tongue is a long muscle utilizing both voluntary and automatic control to combat the natural tendency for gravity to pull the tongue deeper into the throat, thereby complicating respiration in some individuals. While unconscious, this control is purely automatic, and in a substantial number of people with snoring or sleep apnea, resultantly problematic. Without sufficient signaling from the brain to the tongue, the tongue begins to succumb to gravity, thinning the airway for air passage. Tongue sleeve 103 as displayed in FIG. 1(a), as well as the other embodiments disclosed herein, addresses this problem by means of bypassing the need for the tongue to maintain adequate rigidity altogether. In some embodiments wherein the tongue sleeve comprises a suction device, or a device configured to hold the tongue using a suction force, the vacuum created by expelling air from tongue sleeve 103 may serve as a sufficient force countervailing the downward force of gravity on the tongue. As illustrated in FIG. 1(a), tongue 3 is thus moved and kept forward away from the back of the throat.

FIG. 1(b) is a schematic side view of the device illustrated in FIG. 1(a), absent the tongue sleeve, in accordance with one embodiment of the present invention, wherein the tongue sleeve may be removably attached to the mouthpiece. Noticeably, an absent tongue sleeve may result in tongue 3 falling back into the throat—while this may not be an issue to some users, others may not find this option suitable for their needs. As with the embodiment shown in the previous figure, the mouthpiece—comprising maxillary component 101 and mandibular component 102—fits within the confines of the upper lip 1 and lower lip 2. Maxillary component 101 rests superior to tongue 3 and inferior to upper lip 2. Mandibular support rests superior to lower lip 2 and inferior to tongue 3. The user's mandible 5 rests outward from maxilla 4, allowing for the creation of a gap large enough to receive tongue sleeve 103, if so desired by the user. In this illustrated configuration, the tongue sleeve has been removed—as can be seen, even though this configuration may be desirable for some user's, tongue 3 can fall back.

Thus, in one embodiment, tongue sleeve 103 may be detachable from the rest of apparatus 100, leaving the user with a more basic mouthpiece. In such embodiments, the mouthpiece is preferably a mandibular advancement mouthpiece so that the airway may be kept somewhat open even though the tongue can fall back. This feature (i.e., a removable tongue sleeve) may be desirable for use during times in which the user determines his or her snoring and sleep apnea are less severe. This may occur, for example, if the user refrains from alcohol consumption or administration of other muscle relaxants on a particular day. Conversely, if a user typically has little cause for concern over the tongue receding and thereby impeding respiration, but by a change in circumstance the need for tongue sleeve 103 arises, such a user may attach and detach tongue sleeve 103 accordingly. Additionally, with regards to the aforementioned obstacles to intimacy present with current snoring and sleep apnea apparatus, giving a user the choice to opt out of utilizing tongue sleeve 103 when symptoms do not necessitate its use may further compact the present apparatus.

Figure 2A:
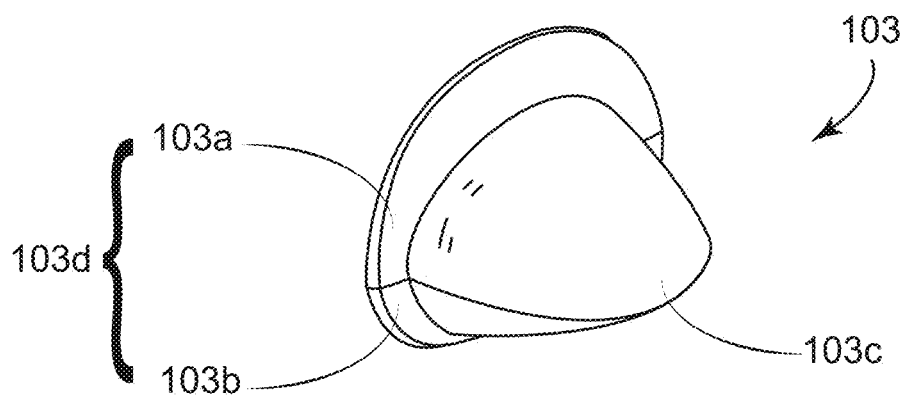
FIG. 2(a) is a perspective view of one embodiment of a tongue sleeve in accordance with the present invention.

Turning now to the next figure, FIG. 2(a) is a perspective view of one embodiment of a tongue sleeve in accordance with the present invention. More specifically, tongue sleeve 103 is shown comprising anchor 103a, anchor 103b, and tongue receiving member 103c, which includes a substantially spherical or semi-spherical protrusion that extends from base 103d, the substantially spherical or semi-spherical protrusion may include an inner surface comprising a concaved cavity suitable for receiving a tip portion of a user's tongue, or tongue tip 3a. Tongue receiving member 103c receives tongue tip 3a and may securely hold tongue tip 3a within the cavity formed by the protrusion using a suction force.

Tongue receiving member 103c of tongue sleeve 103 may be made from an array of materials. For example, and without deviating from the scope of the present invention, tongue receiving member 103c may be constructed using a number of thermoplastics or a surgical or medical grade polymer, such as rubber or the like. Anchor 103a and anchor 103b may be substantially semicircular components together forming base 103d that secures tongue sleeve 103 to the mandibular advancement mouthpiece—that is, to maxillary component 101 and mandibular component 102 of the mouthpiece.

Anchors 103a and 103b may be used to removably attach tongue sleeve 103 to the palatal and lingual aspects of the respective maxillary component 101 and mandibular component 102. In an exemplary embodiment, securement occurs by way of a locking mechanism present on anchors 103a and 103b that each support is configured to receive and subsequently interact with. However, in other embodiments, anchors 103a and 103b may utilize an adhesive material, such as but not limited to: epoxy, sealant, or hot melt. For example, and without limiting the scope of the present invention, an adhesive may be applied to the inner surfaces of anchors 103a and 103b, respectively, to adhere tongue sleeve 103 to maxillary component 101 and mandibular component 102 of the mouthpiece. Moreover, such adhesives may be used to affix tongue sleeve 103 to the mouthpiece either permanently or removably.

Still other embodiments may employ different methods for securement of tongue sleeve 103. For example, tongue sleeve 103 may be removably affixed to maxillary component 101 and mandibular component 102 using a simple locking mechanism such as a mechanism that may snap, slide, or click into place upon proper insertion of tongue sleeve 103 and the mouthpiece.

In various embodiments, tongue sleeve 103 may be malleable insofar as it provides sufficient internal flexibility for comfortable securement of tongue 3, but not malleable enough to enable the user to drastically alter the shape of tongue sleeve 103 whereby any efficacy of the apparatus is lost.

Figure 2B:
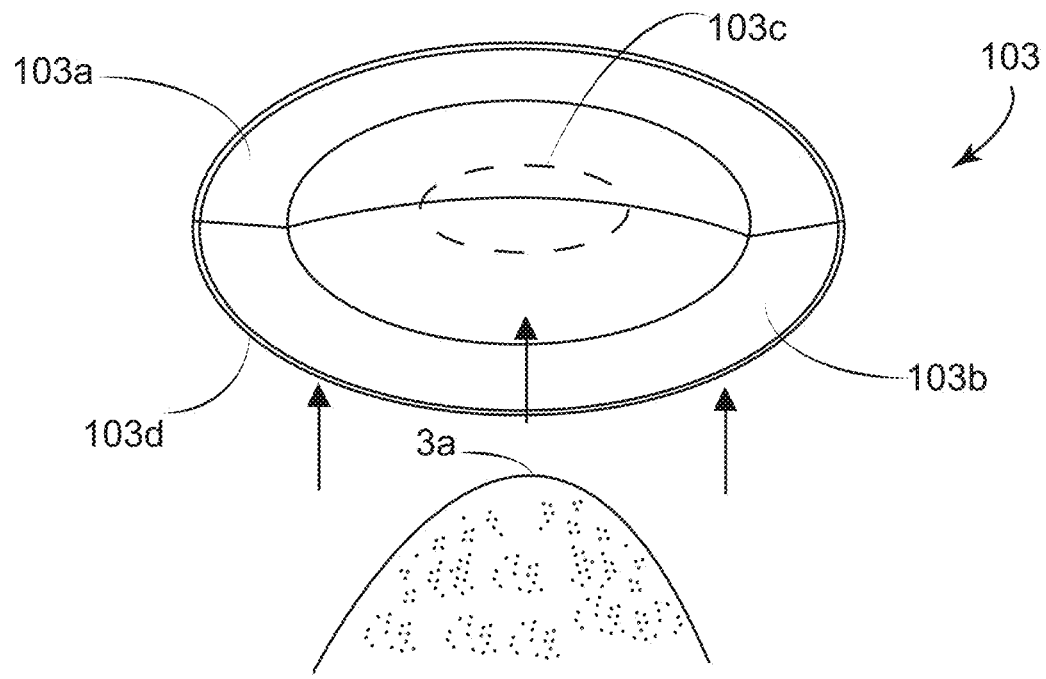
FIG. 2(b) is a back view of the tongue sleeve illustrated in FIG. 2(a).

FIG. 2(b) is a back view of the tongue sleeve illustrated in FIG. 2(a), further illustrating a close-up of a user's tongue moving forward into the confines of the tongue sleeve. In an exemplary embodiment, the tongue sleeve, in accordance with the present invention, may utilize a light suction to adjoin the tongue to the interior of the sleeve. In an exemplary embodiment, air may be first expelled from tongue sleeve 103 by squeezing tongue receiving member 103c— the vacuum created by the expelled air aids in snugly fitting the tongue thereafter. To reverse the process and remove the tongue from tongue sleeve 103, the user again squeezes tongue receiving member 103c. Typically, the tongue approaches tongue receiving member 103c, reserving only enough space for the tip of the tongue to enter. In one embodiment, tongue receiving member 103c comes in a plurality of sizes. In exemplary embodiments, tongue sleeve 103 extends beyond the mouthpiece by as little as 1 or 2 millimeters or as much as 2 centimeters, similarly allowing as little as 1 or 2 millimeters or as much as 2 centimeters of the anterior segment of the tongue to be housed within tongue receiving member 103c. In another embodiment, the tongue-receiving member instead utilizes a gentle clamp which allows for interaction with the mouthpiece to secure the tongue in a configuration further forward than a tongue may typically rest. Alternatively, several sizes may be offered for tongue sleeve 103, whereby a more severe manifestation of snoring or sleep apnea is accompanied by a respective increase in the amount of anterior tongue matter allowably housed in the sleeve.

Figure 3:
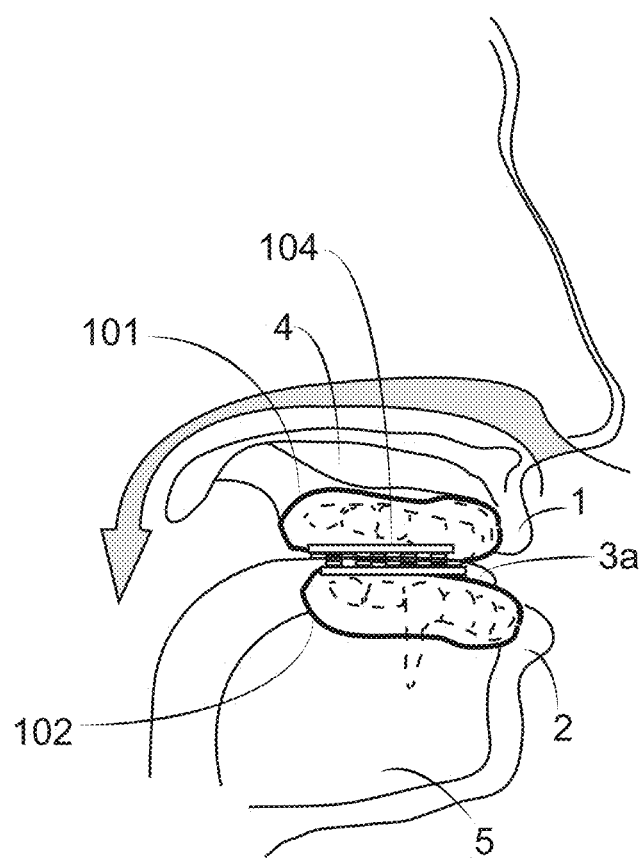
FIG. 3 is a schematic side view of a device incorporating an adjustable mandibular advancement mechanism, in accordance with the present invention.
Figure 4:
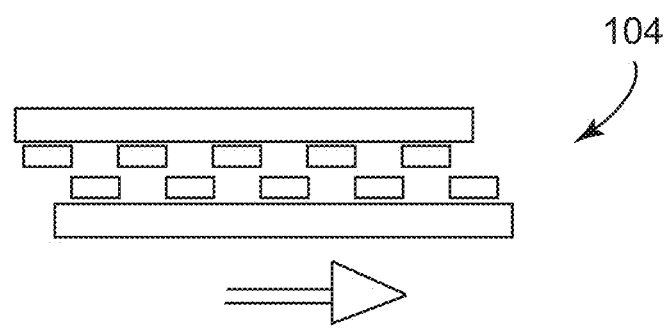
FIG. 4 illustrates how one mandibular advancement mechanism may function in conjunction with a mouthpiece of a dental appliance in accordance with the present invention.

Turning to the next figures, FIG. 3 is a schematic side view of a device incorporating an adjustable mandibular advancement mechanism in accordance with the present invention, and FIG. 4 illustrates how one mandibular advancement mechanism may function in conjunction with a mouthpiece of a dental appliance in accordance with the present invention.

More specifically, FIG. 3 shows a mandibular advancement mouthpiece that incorporates an adjustable mechanism, or mechanism 104. Many mechanisms are known by those skilled in the art for adjusting the disparity of protrusion between a user's mandible 5 and maxilla 4. As such, mechanism 104, as displayed in FIG. 3 and FIG. 4, is merely illustrative and should not be seen as limiting; rather, mechanism 104 is a visual aid for how such a mechanism may be incorporated with the present invention.

In the illustrated embodiment, the mouthpiece of apparatus 100 utilizes mechanism 104, which extends and connects further forward on the mandible side, causing the mandible to be anterior to the maxillary. Mechanism 104 is shown as an interlocking mechanism that may be advanced between a forward and backward position and locked in place.

Again, other mechanisms or means of controlling a desired protrusion of the lower jaw may be implemented without deviating from the scope of the present invention. For example, the mouthpiece itself can be shaped to force the lower jaw forward. In such an embodiment, mechanism 104 would not be necessary. In embodiments where mechanism 104 is not implemented, the mouthpiece may be created from a mold of the user so that the configuration to maximize the desired protrusion may be achieved by a dentist or professional that customizes the mouthpiece to the user's needs. While such an embodiment would not include an adjustable component, such an embodiment may be desirable as a more custom fit design that fits a particular user's needs. FIG. 5(a)-FIG. 10(b) illustrate such embodiments of the present invention, which are discussed in detail below.

Figure 5A:
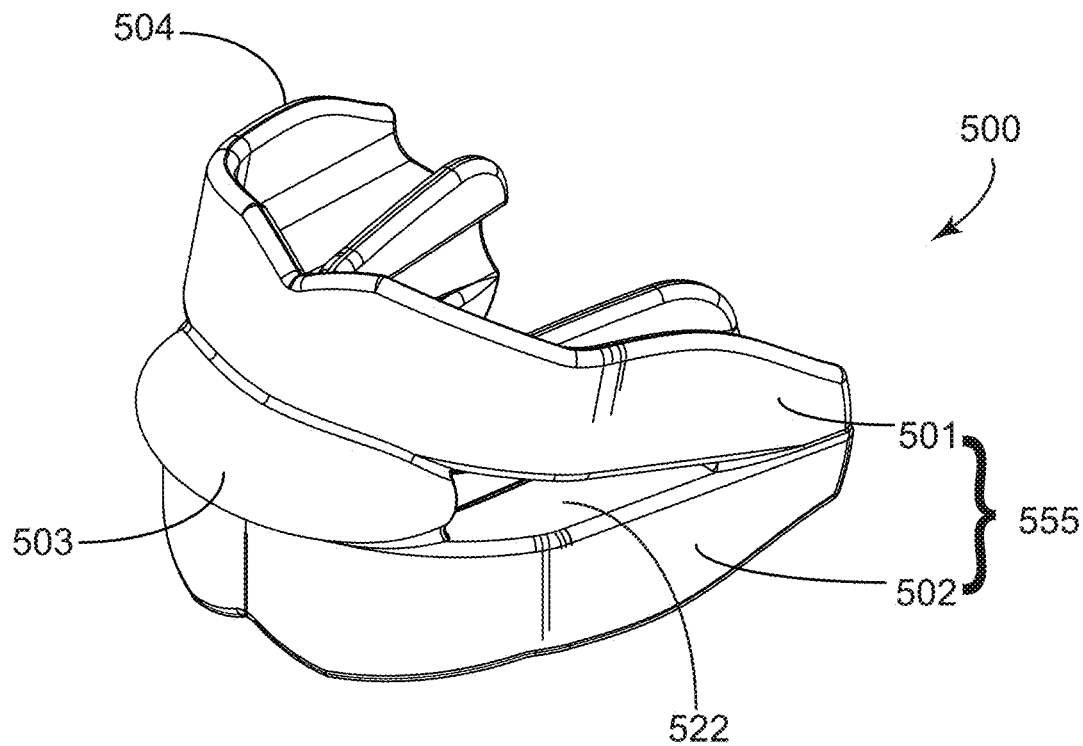
FIG. 5(a) is a perspective view of a dental appliance in accordance with an exemplary embodiment of the present invention.

FIG. 5(a) is a perspective view of a dental appliance in accordance with an exemplary embodiment of the present invention wherein the device includes a tongue sleeve that is permanently attached or integral with the mouthpiece of the dental appliance. Specifically, FIG. 5(a) illustrates dental appliance 500, which includes maxillary component 501, mandibular component 502, and tongue sleeve 503. The maxillary and mandibular components make up what may be referred to as the appliance's mouthpiece, or mouthpiece 555. Tongue sleeve 503 may be situated between maxillary component 501 and mandibular component 502, centered at an anterior end of mouthpiece 555.

In exemplary embodiments, such as is illustrated by dental appliance 500, tongue sleeve 503 is integral with mouthpiece 555. Furthermore, in the shown embodiment, mouthpiece 555 is a mandibular advancement mouthpiece, meaning that mandibular component 502 is situated forward in relation to maxillary component 501 of mouthpiece 555. As explained above, this facilitates keeping a user's airway open by bringing the lower jaw or mandible of a user forward in relation to the maxillary or upper jaw of the user. To help keep a user's tongue from slipping back against the throat and thereby closing the user's airway, tongue sleeve 503 may include a somewhat spherical or semi-spherical portion, comprising a concaved cavity, or interior surface 512, for securely receiving a tip portion of a user's tongue, which protrudes forward from an anterior end of mouthpiece 555.

Figure 5B:
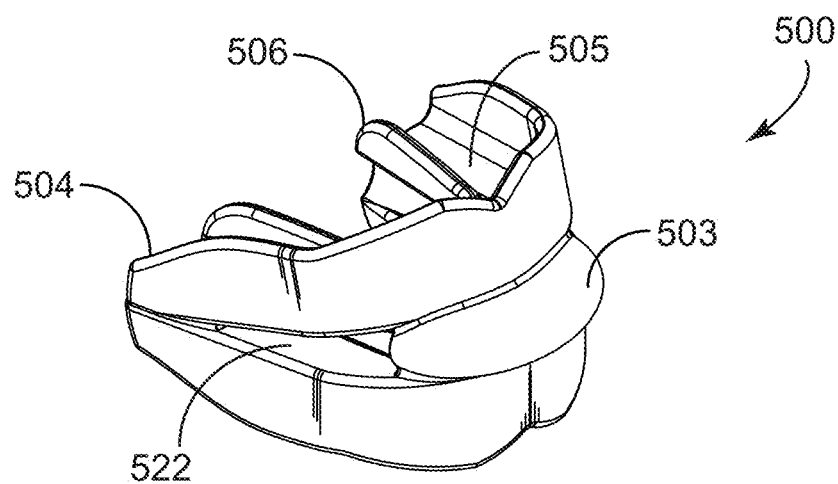
FIG. 5(b) is another perspective view of the dental appliance illustrated in FIG. 5(a) shown from a different angle.

FIG. 5(b) is another perspective view of the dental appliance illustrated in FIG. 5(a) shown from a different angle. As can be seen from the perspective view (somewhat from the top-left side of the device), maxillary component 501 includes a maxillary receptacle (receptacle 505) for receiving the maxillary teeth of a user. Maxillary receptacle 505 includes, or is formed by, an outer ridge 504 and an inner ridge 506. A similar configuration forms the mandibular component of mouthpiece 555, shown in FIG. 6(a) and FIG. 6(b).

Figure 6A:
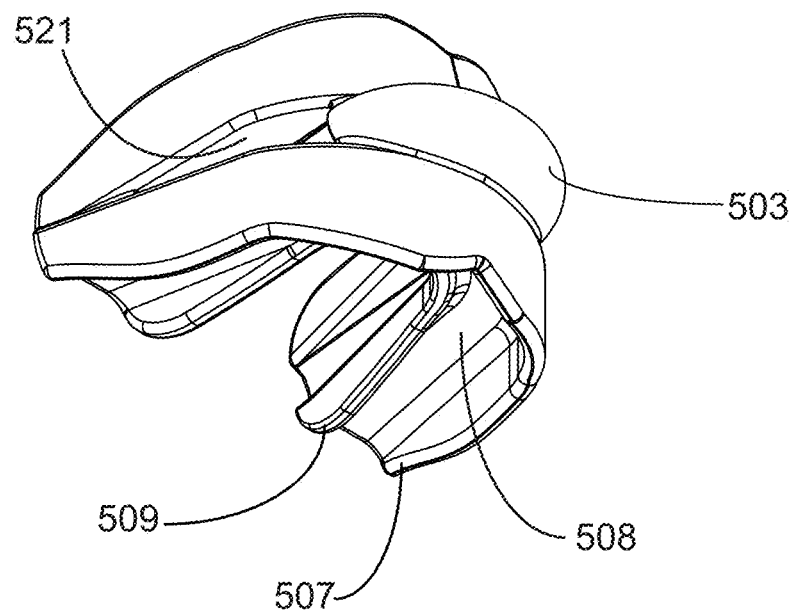
FIG. 6(a) is a perspective view of one embodiment of a dental appliance in accordance with the present invention, showing predominantly the bottom left side of the dental appliance.
Figure 6B:
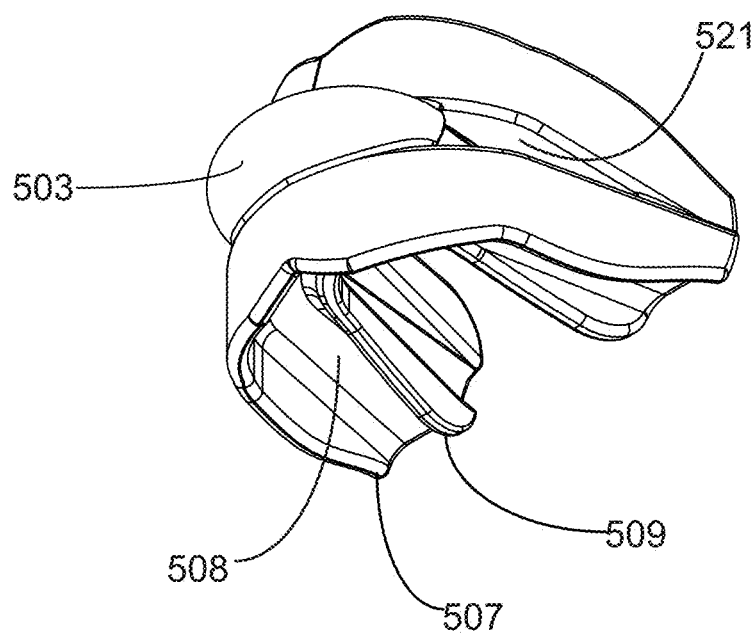
FIG. 6(b) is a perspective view of one embodiment of a dental appliance in accordance with the present invention, showing predominantly the bottom right side of the dental appliance.
Figure 7A:
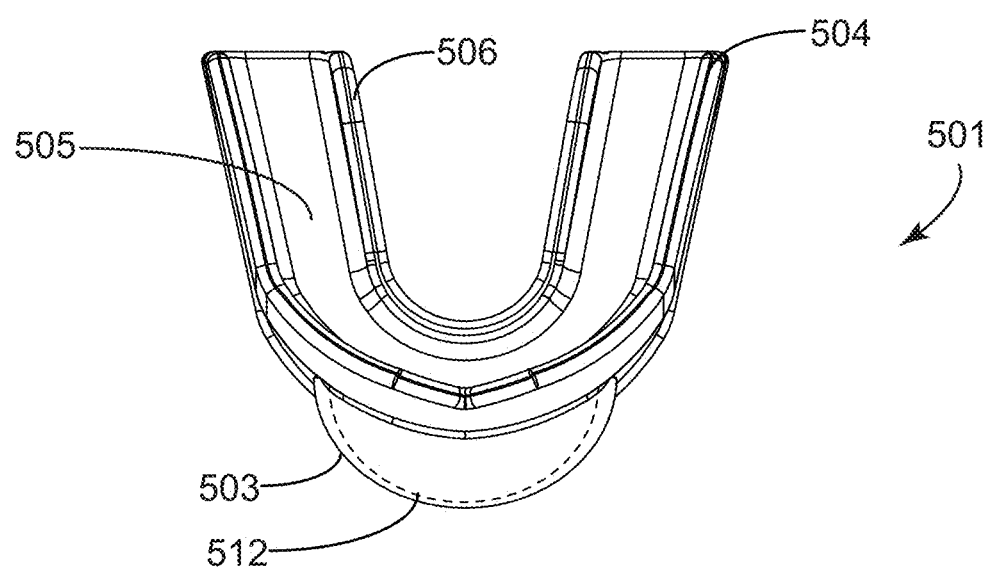
FIG. 7(a) is a top view of a maxillary component of a dental appliance in accordance with the present invention.
Figure 7B:
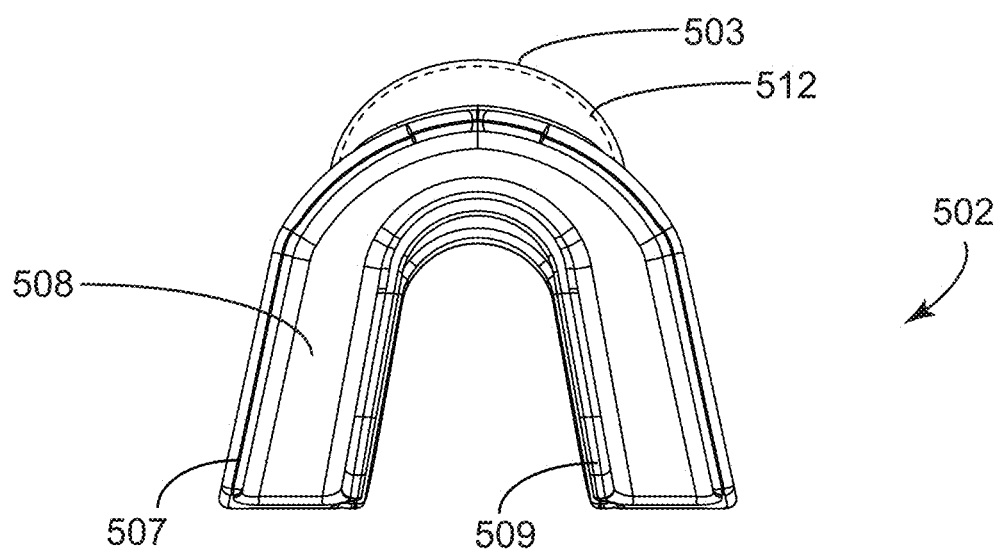
FIG. 7(b) is a bottom view of a mandibular component of a dental appliance in accordance with the present invention.

FIG. 6(a) is a perspective view of one embodiment of a dental appliance in accordance with the present invention showing predominantly the bottom left side of mandibular component 102 of mouthpiece 555, and FIG. 6(b) is a perspective view showing predominantly the bottom right side of mandibular component 102 of mouthpiece 555. Yet other views of both the maxillary receptacle and the mandibular receptacle are further illustrated by FIG. 7(a) and FIG. 7(b); FIG. 7(a) is a top view of maxillary component 501 of dental appliance 500, and FIG. 7(b) is a bottom view of mandibular component 502 of dental appliance 500.

Maxillary component 501 is adapted to receive a user's maxillary teeth and includes outer ridge 504, inner ridge 506, and maxillary receptacle 505 between the outer and inner ridges for receiving the maxillary teeth of the user. Similarly, mandibular component 502 is adapted to receive a user's mandibular teeth and includes outer ridge 507, inner ridge 509, and mandibular receptacle 508 between the outer and inner ridges for receiving the mandibular teeth of the user.

Figure 8A:
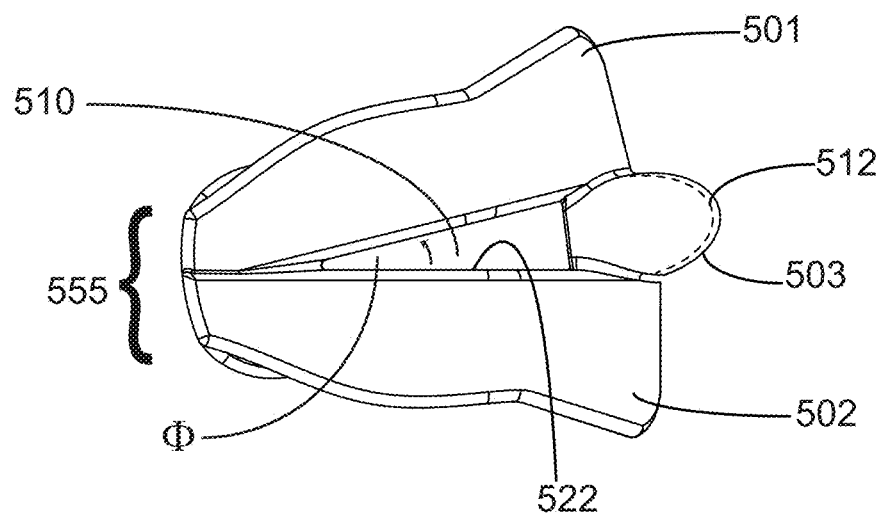
FIG. 8(a) is a side view of one embodiment of a dental appliance in accordance with the present invention, showing the right side of the device.
Figure 8B:
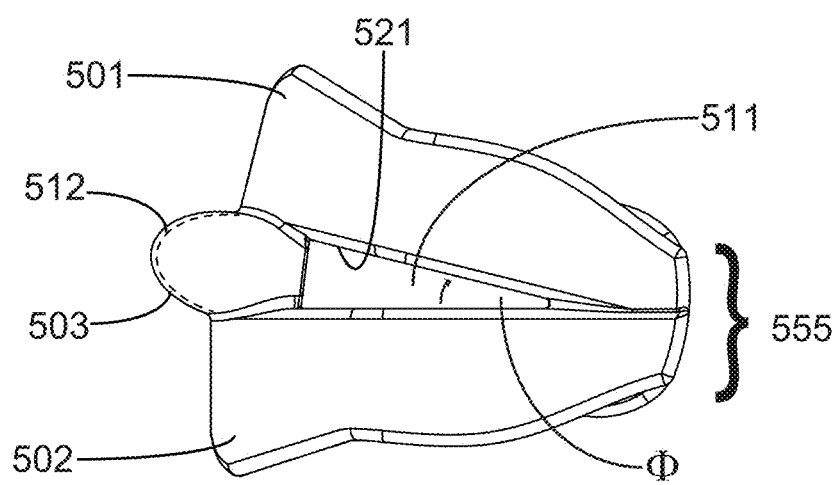
FIG. 8(b) is a side view of one embodiment of a dental appliance in accordance with the present invention, showing the left side of the device.

Turning to the next figures, FIG. 8(a) is a side view of dental appliance 500, and FIG. 8(b) is another side view, showing the other side of the dental appliance. More specifically, an exemplary embodiment of dental appliance 500 is shown, wherein maxillary component 501 and mandibular component 502 of the mandibular advancement mouthpiece form an acute angle $\Phi$ with its vertex at a posterior region of the mandibular advancement mouthpiece 555. Moreover, the substantially spherical or semi-spherical portion of tongue sleeve 503 is situated opposite the vertex of the acute angle formed at the posterior junction between the maxillary and mandibular components 501 and 502. In this configuration, mouthpiece 555 includes one or more openings for enabling airflow between an exterior and interior of the mouthpiece. That is, openings 510 and 511 allow a user to breathe through their mouth while the dental appliance is in use and the user's tongue is securely placed in tongue sleeve 503. Openings 510 and 511 may be implemented into dental appliance 500 in any number of ways. In the exemplary embodiment shown, the openings are located at either side of tongue sleeve 503, and more particularly, the openings may be implemented so that a first opening is situated to the right of the tongue sleeve and a second opening is situated to the left of the tongue sleeve, wherein both the first and second openings are situated between the maxillary and mandibular components of the mouthpiece.

Figure 9:
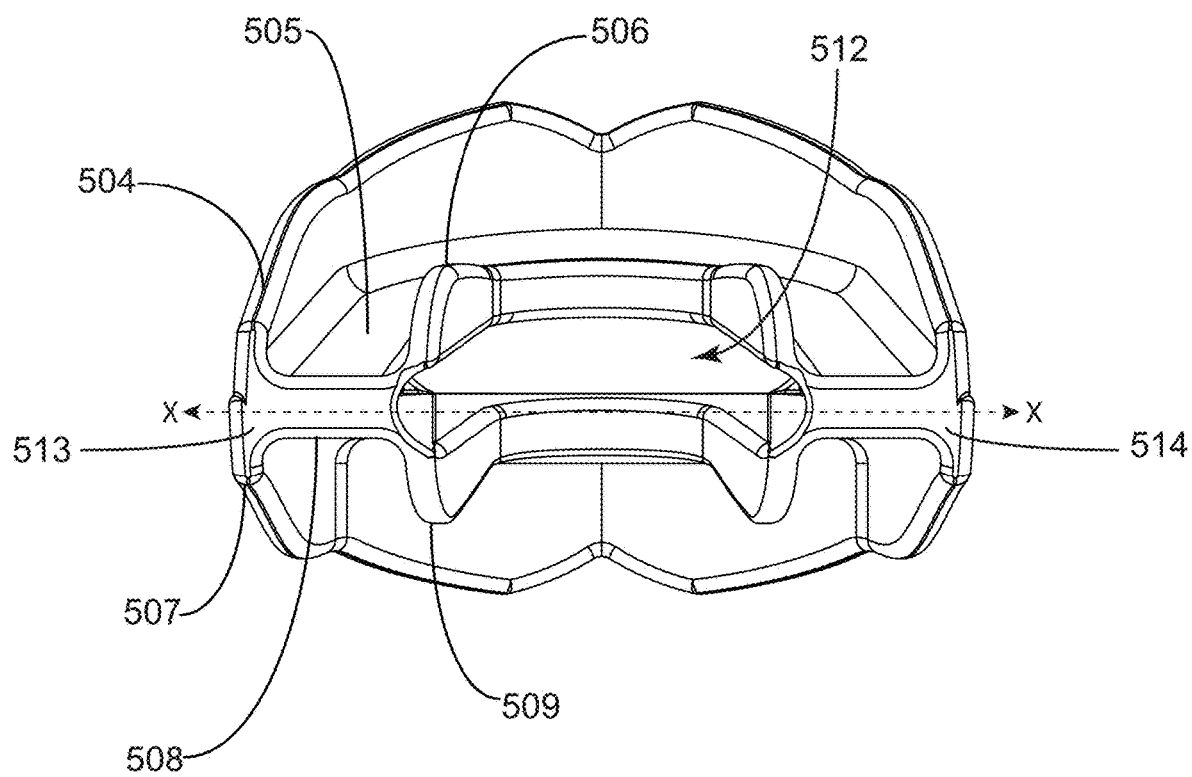
FIG. 9 is a back view of one embodiment of a dental appliance in accordance with the present invention.

Turning to the next figure, FIG. 9 is a back view of dental appliance 500, on which line X is imposed to denote the top and bottom portions of the dental appliance. Specifically, the top portion of line X includes a back view of maxillary component 501 with outer ridge 504 lining the entire top outer region of maxillary component 501, and inner ridge 506 lining the entire top inner region of maxillary component 501. In between outer region 504 and inner region 506 lies receptacle 505, which is the region adapted to receive a user's maxillary teeth. Similarly, the bottom portion of line X includes a back view of mandibular component 502 with outer ridge 507 lining the entire bottom outer region of mandibular component 502, and inner ridge 509 lining the entire bottom inner region of mandibular component 502. In between outer region 507 and inner region 509 lies receptacle 508, which is the region adapted to receive a user's mandibular teeth.

Typically, a user's tongue lies in the center region of the dental appliance and may be placed or inserted into tongue sleeve 503 so that a tip portion of a user's tongue may contact the interior surface of tongue sleeve 503, or interior surface 512. From the back view illustrated by FIG. 9, it may be appreciated that in one embodiment, maxillary component 501 and mandibular component 502 may be connected at the vertex of the angle their junction forms, or vertices 513 and 514.

Figure 10A:
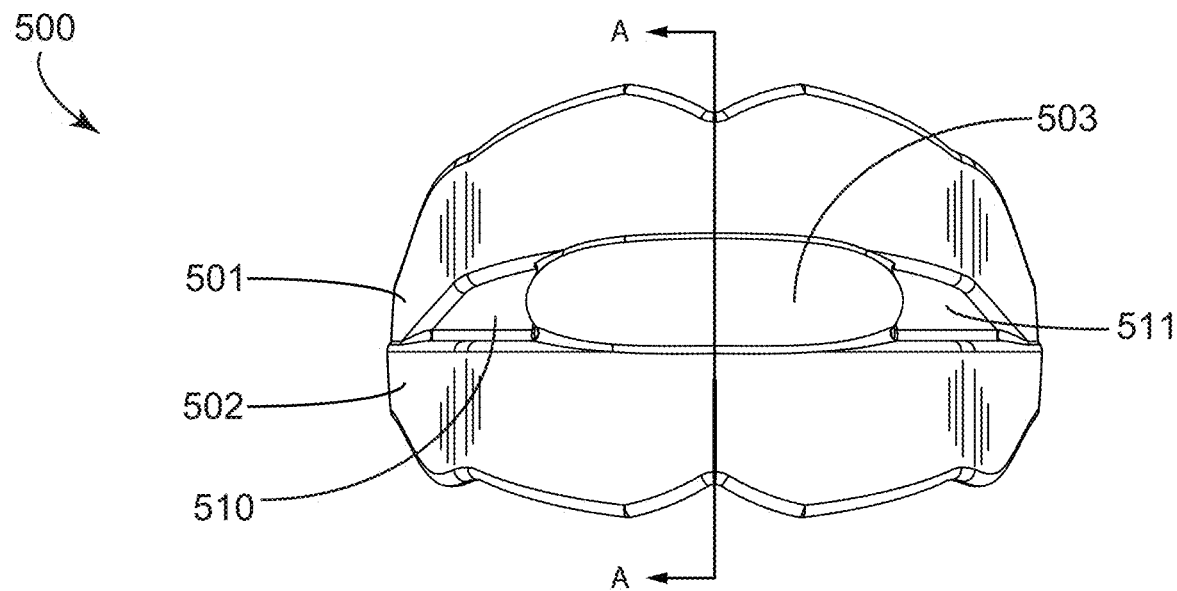
FIG. 10(a) is a front view of one embodiment of a dental appliance in accordance with the present invention.
Figure 10B:
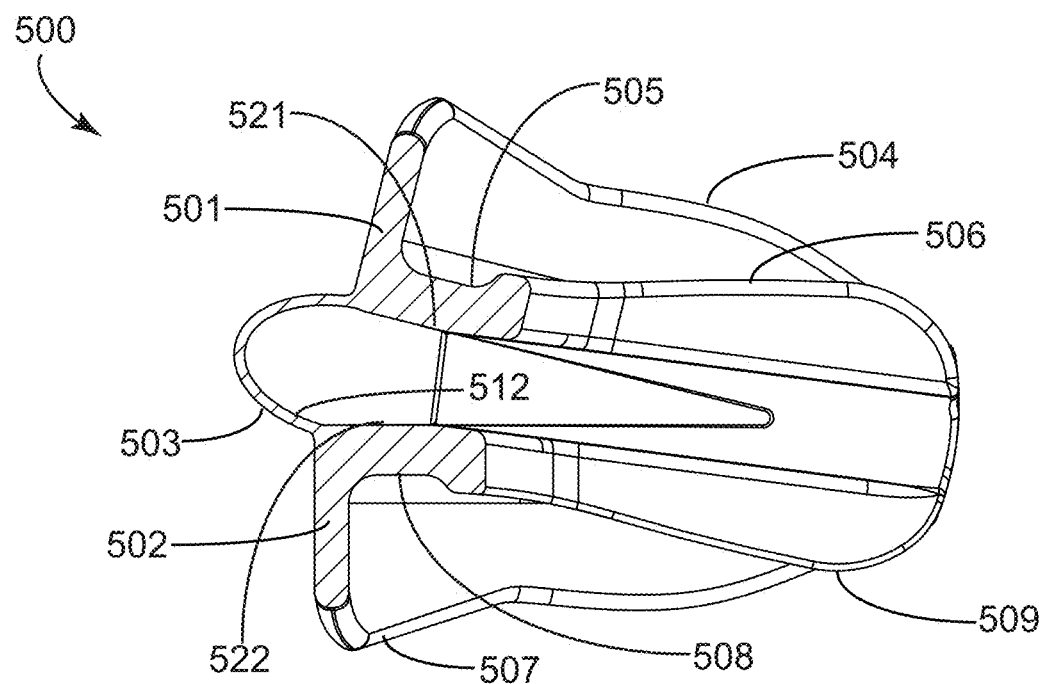
FIG. 10(b) is a cross sectional view of one embodiment of the dental appliance shown in FIG. 10(a), the cross section taken at line A.

Turning to the next figures, FIG. 10(a) depicts a front view of dental appliance 500, wherein openings 510 and 511 are substantially situated at a front portion of dental appliance 500. FIG. 10(b) is a cross sectional view of dental appliance 500, wherein a cross section is taken at line A.

Opening 510 (on the right side of dental appliance 500) and opening 511 (on the left side of dental appliance 500) provide airflow for full mouth breathing by the user. Of course, other types of openings may be implemented so long as they are suitable for allowing a user to breathe through their mouth, for example during sleep; this is desirable as a user with conditions such as sleep apnea or severe snoring often cannot properly breathe through their nose.

Maxillary component 501 and mandibular component 502 of mouthpiece 555 are typically constructed of medical-grade polymers or copolymers that may be custom fit to a user's specifications. In exemplary embodiments, the materials used to construct mouthpiece 555 allow easy cleaning of dental appliance 500. Furthermore, soft or somewhat malleable materials may be implemented so that maxillary component 501 and mandibular component 502 may cushion a user's teeth during sleep. Different materials may be used without deviating from the scope of the invention, including for example materials that prevent or reduce teeth from grinding against the maxillary and mandibular components of mouthpiece 555.

For example, and without limiting the scope of the present invention, maxillary receptacle 505 and mandibular receptacle 508 may include a soft malleable surface so that teeth may be cushioned therein. Of course, the materials used to construct dental appliance 500 desirably provide a rigid aspect to the device so that a user is prevented from completely shutting their jaw during sleep. For example, while maxillary receptacle 505 and mandibular receptacle 508 may include softer malleable materials, the remainder of the dental appliance 500 may include harder, more rigid plastics that keep maxillary component 501 and mandibular component 502 at a fixed angle Φ at vertices 513 and 514. This way, the user's tongue may be continuously held in place inside tongue sleeve 503, thereby preventing the user's tongue from falling back to the user's throat.

Tongue sleeve 503 is integral with mouthpiece 555 and connects maxillary component 501 and mandibular component 502 at the front or anterior end of dental appliance 500. Hence, as can be appreciated in FIG. 10(b), maxillary component 501 and mandibular component 502 may be joined at an anterior end of dental appliance 500 (i.e., by tongue sleeve 503), as well as at a posterior end of dental appliance 500 (i.e., by vertices 513 and 514). In exemplary embodiments, tongue sleeve 103 may extend beyond mouthpiece 555 by as little as 1 or 2 millimeters or as much as 2 centimeters, similarly allowing as little as 1 or 2 millimeters or as much as 2 centimeters of the anterior segment of the tongue to be housed within tongue sleeve 503.

Tongue sleeve 503 may include any shape that is suitable for receiving a user's tongue. In one embodiment, tongue sleeve 503 protrudes from an anterior and lower portion of maxillary component 501 and from an anterior and upper portion of mandibular component 502, tongue sleeve 503 extending outward from both components to form a semi-spherical shape on the exterior and front portion of dental appliance 500. In the interior of tongue sleeve 503, a complementary concaved surface, or inner surface 512, may be formed. Inner surface 512 may be suitable for receiving the anterior or tip portion of a user's tongue, and in some embodiments, may comprise a composition or texture that maximizes a suction force for retaining or securely holding a user's tongue within tongue sleeve 503.

As may be gleaned from the several views in the figures, the interior portions of mouthpiece 555, or inner surface 521 and inner surface 522, are in one embodiment flat. This allows for the openings to maximize airflow between the interior and exterior of the device.

Figure 11A:
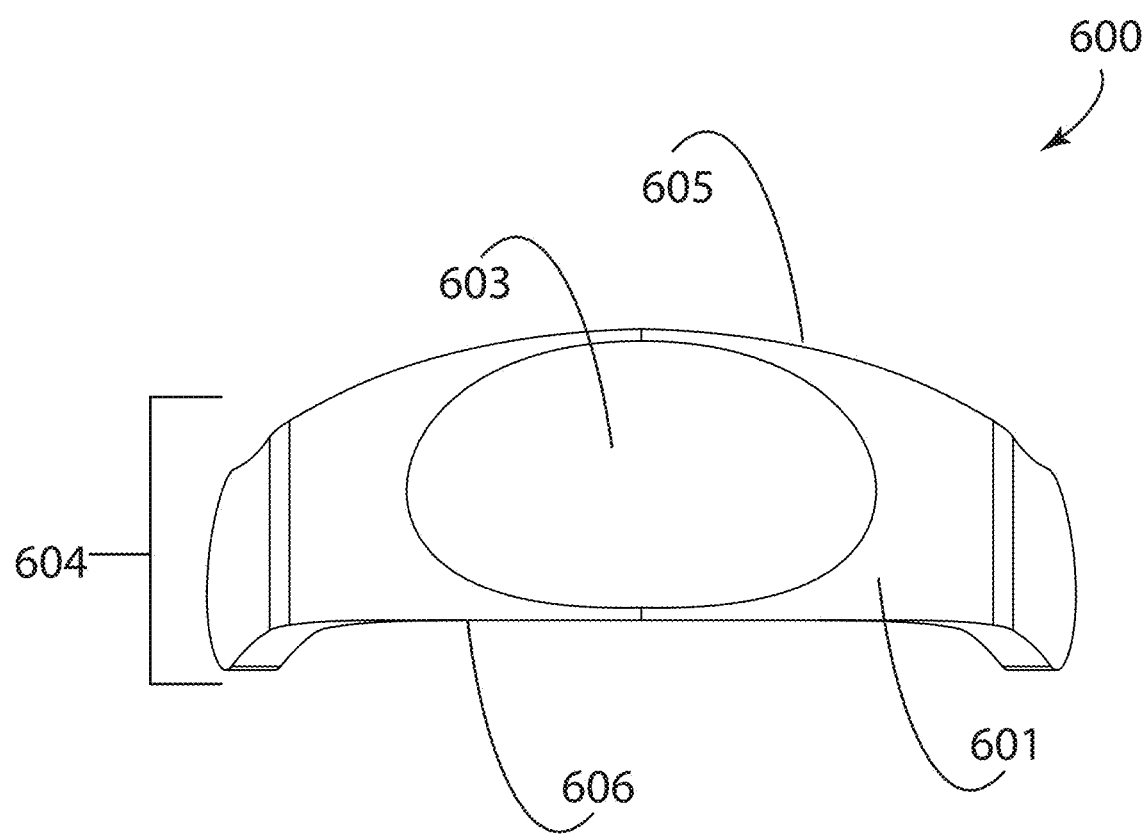
FIG. 11(a) is a front view of one embodiment of a dental appliance in accordance with the present invention.
Figure 11B:
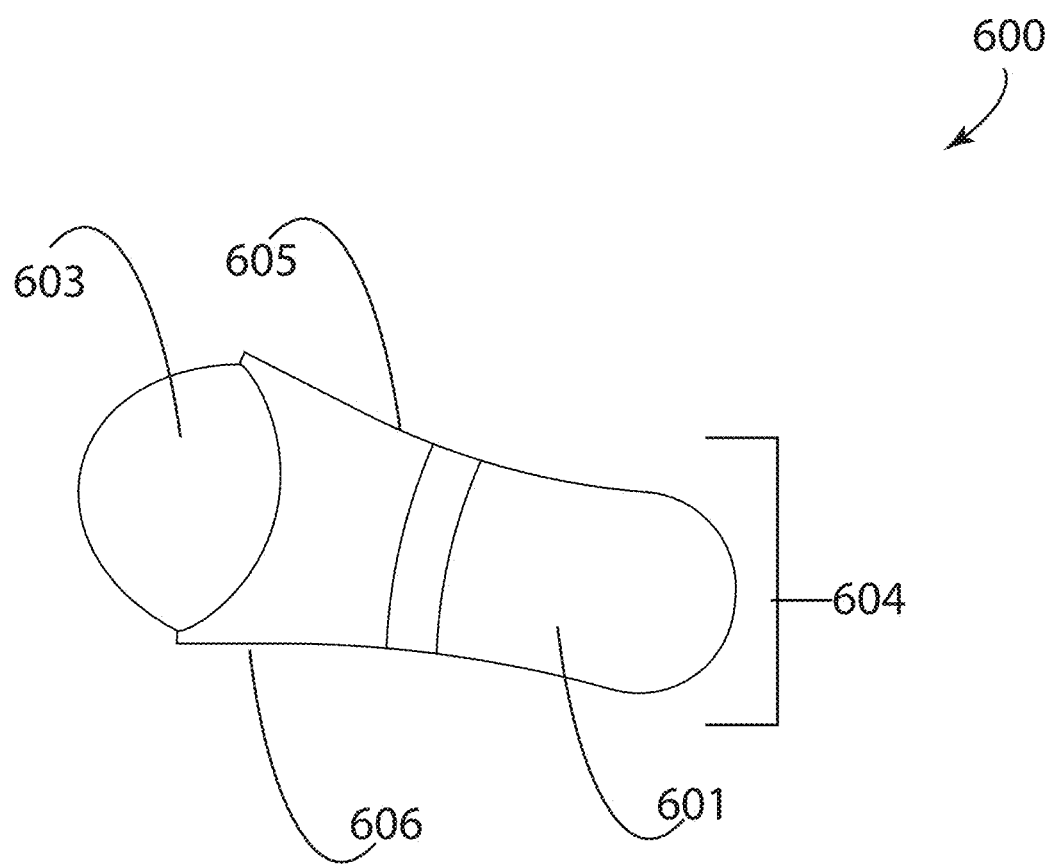
FIG. 11(b) is a side view of one embodiment of a dental appliance in accordance with the present invention, showing the left side of the device.
Figure 11C:
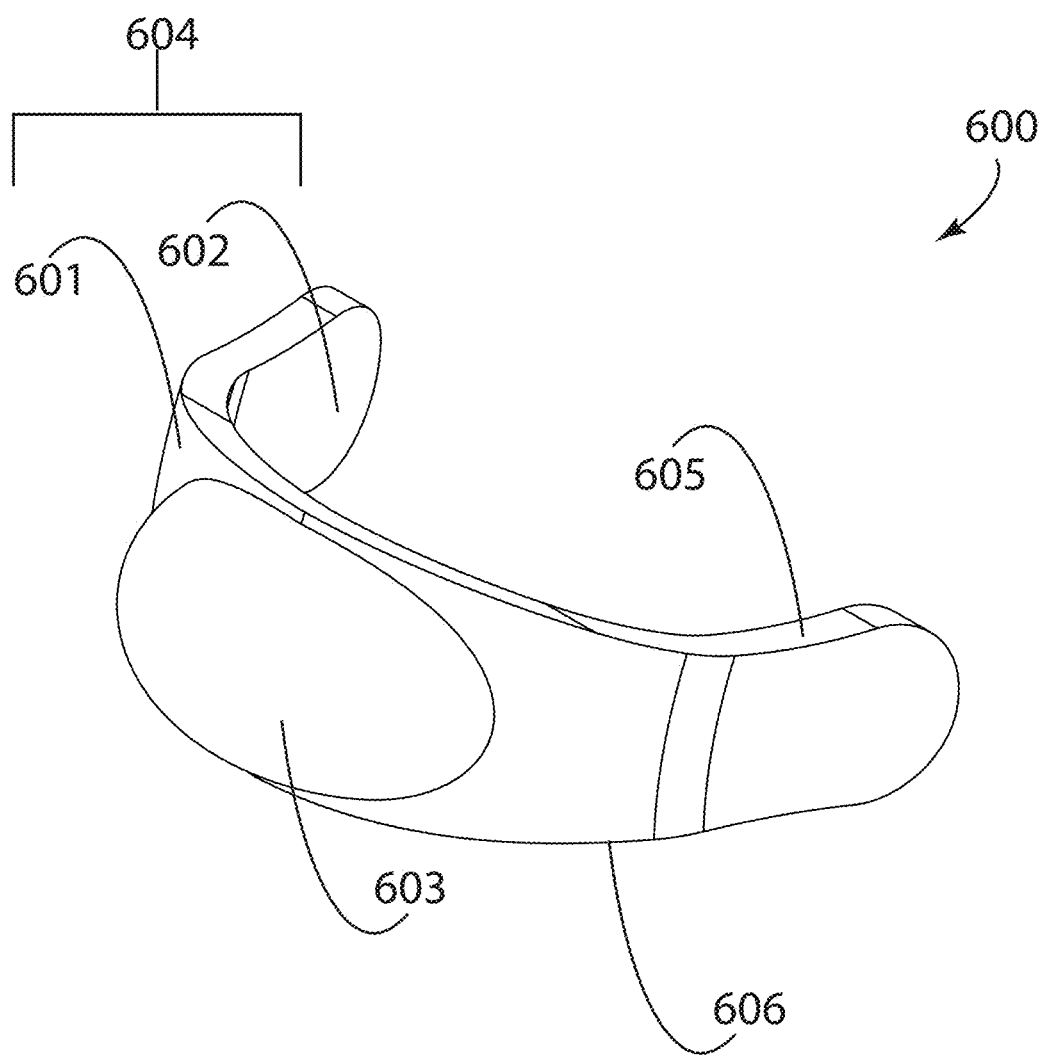
FIG. 11(c) is a perspective view of one embodiment of a dental appliance in accordance with the present invention.
Figure 11D:
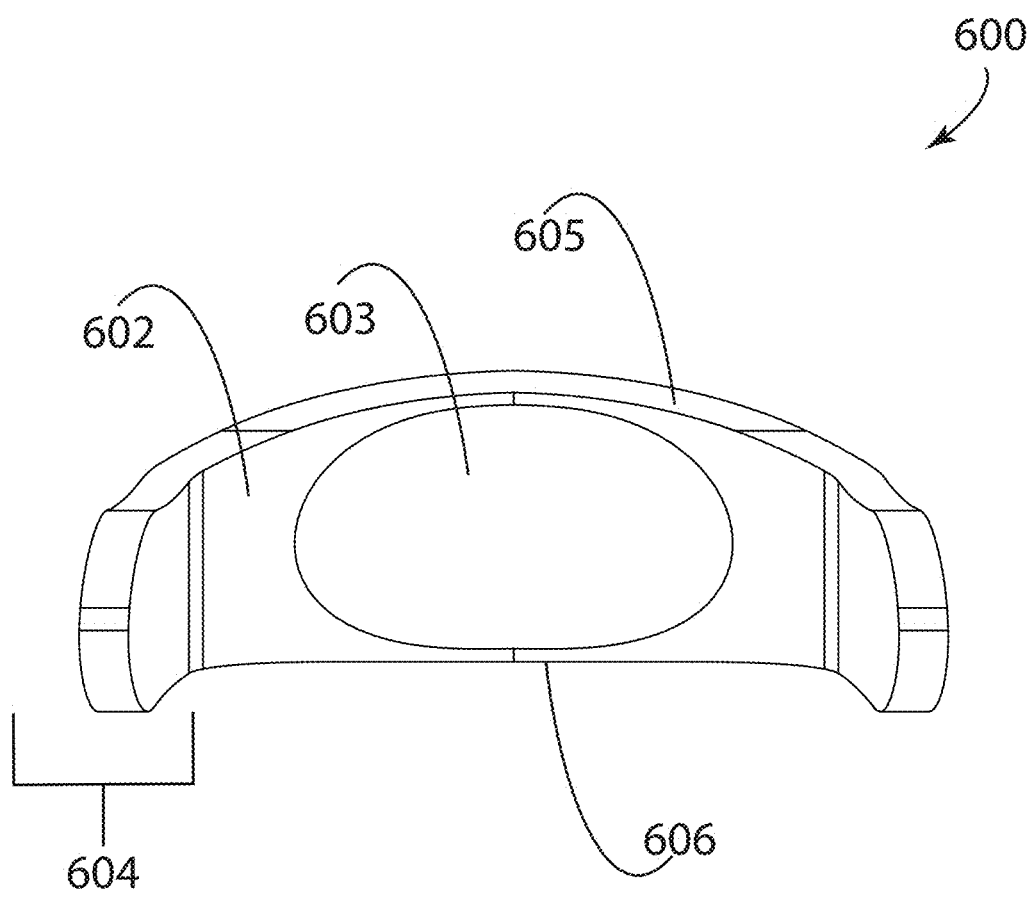
FIG. 11(d) is a back view of one embodiment of a dental appliance in accordance with the present invention.

Turning to the next figure, FIG. 11(a) depicts a front view of a dental appliance in accordance with one embodiment of the present invention, wherein the device includes a tongue sleeve that may be integral with the mouthpiece of the dental appliance. Specifically, FIG. 11(a) illustrates dental appliance 600, which includes exterior surface 601, interior surface 602 (See FIGS. 11(c) and 11(d)), and tongue sleeve 603. Exterior surface 601 and interior surface 602 make up what may be referred to as mouthpiece 604. Mouthpiece 604 may have an upper surface 605 and a lower surface 606. Unlike a CPAP machine, dental appliance 600, of which a plurality of embodiments is disclosed herein, produces no audible sound since it does not require a machine or motor, and as such does not impede restful sleep for the user or those nearby. Moreover, dental appliance 600 includes tongue sleeve 603, which uniquely functions to keep the user's tongue in a position that allows for the user's airway to remain open.

In exemplary embodiments, such as is illustrated by dental appliance 600, tongue sleeve 603 may be integral with mouthpiece 604. Tongue sleeve 603 may be located equidistant from upper surface 605 and lower surface 606 such that mouthpiece 604 circumscribes tongue sleeve 603.

It is envisioned that the entirety of dental appliance 600 may fit inside a user's mouth within the confines of the user's upper and lower lips, similar to a sport's mouthpiece. By way of example and not limitation, a user may secure their tongue within tongue sleeve 603 and secure mouthpiece 604 by placing their upper lip on top of or over upper surface 605 and their lower lip under lower surface 606. Such a use of dental appliance 600 would allow a user's teeth and lips to prevent the dental appliance 600 from falling out of or further into the user's mouth while the user slept.

The material from which mouthpiece 604 may be constructed is not to be limited. For example, and without limitation, mouthpiece 604 may be comprised of a number of types of polymers, copolymers, or plastics, such as thermoplastics, as well as harder materials such as gold or acrylic, or alloys composed of such materials as cobalt or chrome. Alternatives to the enumerated materials should be apparent to those skilled in the art.

Integral with mouthpiece 604 is tongue sleeve 603. Tongue sleeve 603 receives a user's tongue and securely holds the tongue in a forward configuration relative to the user's mouth. Tongue sleeve 603 serves as a tongue-receiving member or the component that securely receives a tip portion of the user's tongue. Tongue sleeve 603 may comprise multiple components or a single component without deviating from the scope of the present invention. For example, tongue sleeve 603 may be a clamping device, a suction device, or any general retaining device. In one embodiment, tongue sleeve 603 comprises a flexible, substantially spherical or semi-spherical protrusion including an inner surface comprising a concaved portion devoid of openings suitable for receiving a tip portion of the user's tongue. In such an embodiment, tongue sleeve 603 may implement suction to keep the tongue securely within tongue sleeve 603.

FIG. 11(*b*) is a side view of a dental appliance in accordance with one embodiment of the present invention. As may be better illustrated by this figure, tongue sleeve 603 may be integral with mouthpiece 604. Of course, it is also envisioned that tongue sleeve 603 may be removably attached to mouthpiece 604. Being removably attached may allow a user to easily and more thoroughly clean tongue sleeve 603. This feature (i.e., a removable tongue sleeve 603) may be desirable for use during times in which the user determines his or her snoring and sleep apnea are less severe. This may occur, for example, if the user refrains from alcohol consumption or administration of other muscle relaxants on a particular day. Conversely, if a user typically has little cause for concern of the tongue receding and thereby impeding respiration, but by a change in circumstance the need for tongue sleeve 603 arises, such a user may attach and detach tongue sleeve 603 accordingly. Additionally, with regards to the aforementioned obstacles to intimacy present with current snoring and sleep apnea apparatus, giving a user the choice to opt out of utilizing tongue sleeve 603 when symptoms do not necessitate its use may further compact the present apparatus.

In some embodiments of the present invention, tongue sleeve 603 may be secured to mouthpiece 604 by utilizing an adhesive material, such as but not limited to: epoxy, sealant, hot melt, or any other suitable adhesive. Such adhesives may be used to affix tongue sleeve 603 to mouthpiece 604 either permanently or removably.

Still other embodiments may employ different methods for securing tongue sleeve 603. For example, tongue sleeve 603 may be removably affixed to mouthpiece 604 using a simple locking mechanism such as a mechanism that may snap, slide, or click into place upon proper insertion of tongue sleeve 603 into mouthpiece 604.

In various embodiments, tongue sleeve 603 may be malleable insofar as it provides sufficient internal flexibility for comfortable securement of the user's tongue, but not malleable enough to enable the user to drastically alter the shape of tongue sleeve 603 whereby any efficacy of dental appliance 600 is lost.

In an exemplary embodiment of the present invention, the shape of mouthpiece 604 may be curved at an angle. For example, and without limitation, a center portion of upper surface 605 and a center portion of lower surface 606 may curve inwardly toward a center portion of mouthpiece 604. Curving upper surface 605 and lower surface 606 in this manner may cause mouthpiece 604 to have an exaggerated shape which may be similar to the shape of the user's mouth. The exaggerated shape may help retain mouthpiece 604 within the user's mouth.

Turning to the next figure, FIG. 11(*c*) illustrates a perspective view of a dental appliance in accordance with one embodiment of the present invention. As may be better appreciated by this figure, exterior surface 601 and interior surface 602 of mouthpiece 604 may be completely smooth and devoid of openings or protrusions (save for where tongue sleeve 603 may connect to mouthpiece 604). However, in other embodiments of the present invention, exterior surface 601 and interior surface 602 may be comprised of a plurality of perforations without deviating from the spirit and scope of the present invention. Such perforations may allow a user to increase their intake of oxygen while using the dental appliance 600.

FIG. 11(*d*) is a back view of the tongue sleeve. In an exemplary embodiment, tongue sleeve 603, in accordance with the present invention, may utilize a light suction to adjoin the tongue to the interior of tongue sleeve 603. In an exemplary embodiment, air may first be expelled from tongue sleeve 603 by squeezing tongue sleeve 603—the vacuum created by the expelled air may aid in securing the tongue thereafter. To reverse the process and remove the tongue from tongue sleeve 603, the user may again squeeze tongue sleeve 603. Typically, the tongue approaches tongue sleeve 603, reserving only enough space for the tip of the tongue to enter. In one embodiment, tongue sleeve 603 may come in a plurality of sizes. In exemplary embodiments, tongue sleeve 603 extends beyond mouthpiece 604 by as little as 1 or 2 millimeters or as much as 2 centimeters, similarly allowing as little as 1 or 2 millimeters or as much as 2 centimeters of the anterior segment of the tongue to be housed within tongue sleeve 603. Alternatively, several sizes may be offered for tongue sleeve 603, whereby a more severe manifestation of snoring or sleep apnea is accompanied by a respective increase in the amount of anterior tongue matter allowably housed in tongue sleeve 603.

In another embodiment, tongue sleeve 603 may instead utilize a gentle clamp which allows for interaction with mouthpiece 604 to secure the tongue in a configuration further forward than a tongue may typically rest.

Figure 12A:
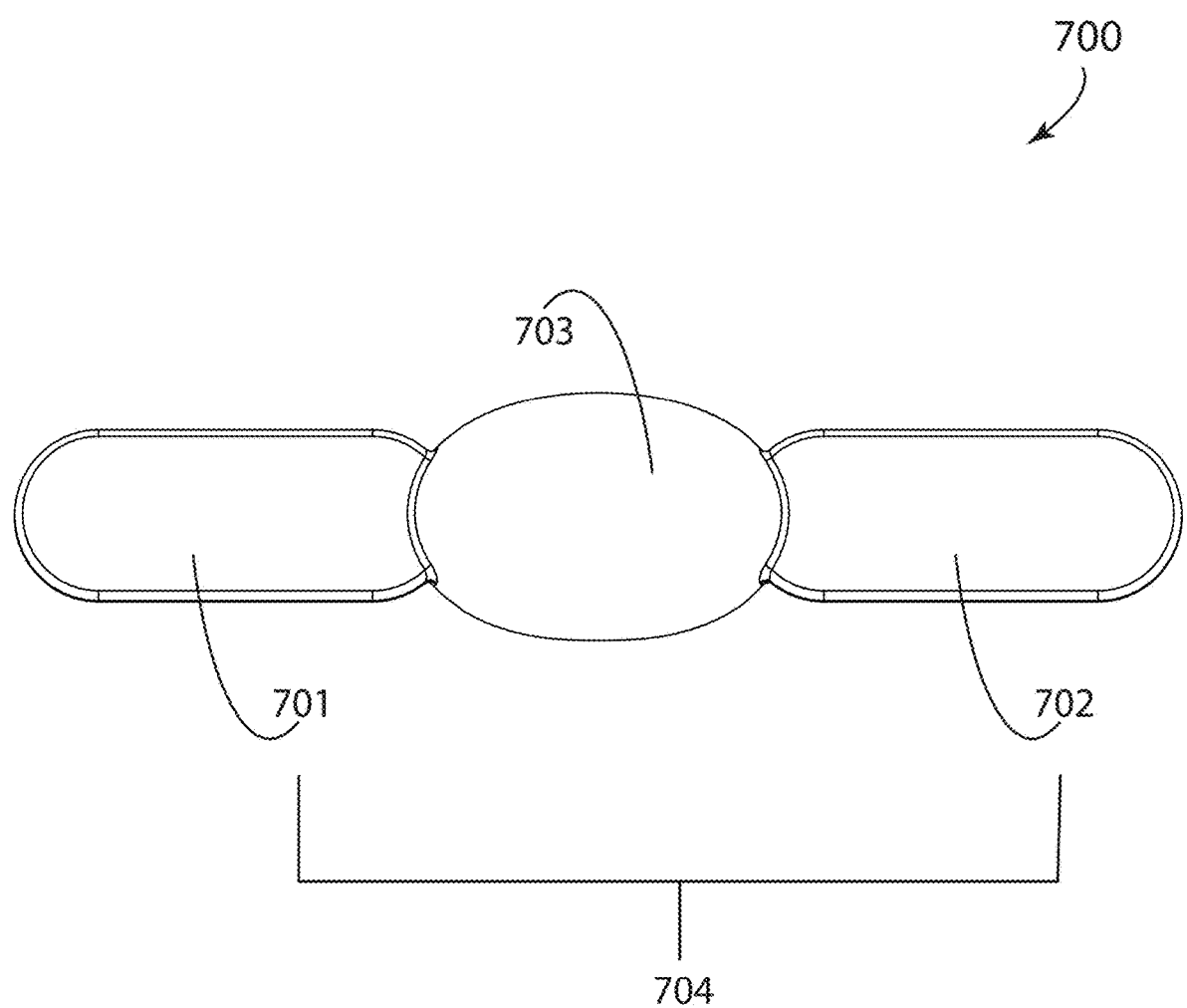
FIG. 12(a) is a front view of one embodiment of a dental appliance in accordance with the present invention.

Turning now to the next figure, FIG. 12(a) is a front view of a dental appliance in accordance with one embodiment of the present invention. Specifically, FIG. 12(a) illustrates dental appliance 700, which includes first arm 701, second arm 702, and tongue sleeve 703. First arm 701 and second arm 702 make up what may be referred to as mouthpiece 704. Unlike a CPAP machine, dental appliance 700, of which a plurality of embodiments is disclosed herein, produces no audible sound since it does not require a machine or motor. Moreover, dental appliance 700 includes tongue sleeve 703, which uniquely functions to keep the user's tongue in a position that allows for an airway to remain open.

In exemplary embodiments, such as is illustrated by dental appliance 700, tongue sleeve 703 may be integral with mouthpiece 704. Tongue sleeve 703 may be located between and removably attached to first arm 701 and second arm 702.

It is envisioned that first arm 701 and second arm 702 of dental appliance 700 may rest on top of and extend outwardly from a user's mouth when the user's tongue is inserted into tongue sleeve 703. By way of example and not limitation, a user may secure their tongue within tongue sleeve 703 and secure mouthpiece 704 by placing their tongue within a concaved cavity of tongue sleeve 703. The concaved cavity of tongue sleeve 703 may have an interior concaved surface devoid of openings. First arm 701 and second arm 702 may serve to maintain dental appliance 700 in a desired position.

The material from which first arm 701 and second arm 702 may be constructed is not to be limited. For example, and without limitation, first arm 701 and second arm 702 may be comprised of a number of types of polymers, copolymers, or plastics, such as thermoplastics, as well as harder materials such as gold or acrylic, or alloys composed of such materials as cobalt or chrome. Alternatives to the enumerated materials should be apparent to those skilled in the art.

Situated between first arm 701 and second arm 702 is tongue sleeve 703. Tongue sleeve 703 may receive a user's tongue and securely hold the tongue in a forward configuration relative to the user's mouth. Tongue sleeve 703 may comprise multiple components or a single component without deviating from the scope of the present invention. For example, tongue sleeve 703 may be a clamping device, a suction device, or any general retaining device. In one embodiment, tongue sleeve 703 comprises a flexible, substantially spherical or semi-spherical protrusion including an inner surface comprising a concaved portion suitable for receiving a tip portion of the user's tongue. In such an embodiment, tongue sleeve 703 may implement suction to keep the tongue securely within tongue sleeve 703.

Figure 12B:
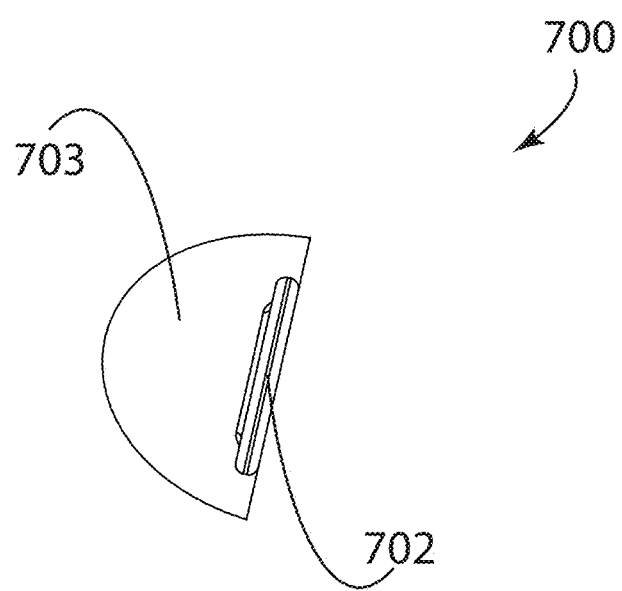
FIG. 12(b) is a side view of one embodiment of a dental appliance in accordance with the present invention.

FIG. 12(b) is a side view of a dental appliance in accordance with one embodiment of the present invention. As may be better illustrated by this figure, tongue sleeve 703 may be integral with mouthpiece 704. Of course, it is also envisioned that tongue sleeve 703 may be removably attached to mouthpiece 704. This feature (i.e., a removable tongue sleeve 703) may be desirable for use during times in which the user determines his or her snoring and sleep apnea are less severe. Conversely, if a user typically has little cause for concern of the tongue receding and thereby impeding respiration, but by a change in circumstance the need for tongue sleeve 703 arises, such a user may attach and detach tongue sleeve 703 accordingly.

In some embodiments of the present invention, tongue sleeve 703 may be secured to mouthpiece 704 by utilizing an adhesive material, such as but not limited to: epoxy, sealant, hot melt, or any other suitable adhesive. Such adhesives may be used to removably or permanently affix tongue sleeve 703 to mouthpiece 704.

Still other embodiments may employ different methods for securing tongue sleeve 703. For example, tongue sleeve 703 may be removably affixed to mouthpiece 704 using a simple locking mechanism such as a mechanism that may snap, slide, or click into place upon proper insertion of tongue sleeve 703 into mouthpiece 704.

In various embodiments, tongue sleeve 703 may be malleable insofar as it provides sufficient internal flexibility for comfortable securement of the user's tongue, but not so malleable as to enable the user to drastically alter the shape of tongue sleeve 703 whereby any efficacy of dental appliance 700 is lost.

Typically, tongue sleeve 703 may reserve only enough space for the tip of the tongue to enter. In one embodiment, tongue sleeve 703 may come in a plurality of sizes. In exemplary embodiments, tongue sleeve 703 may extend beyond mouthpiece 704 by as little as 1 or 2 millimeters or as much as 2 centimeters, similarly allowing as little as 1 or 2 millimeters or as much as 2 centimeters of the anterior segment of the tongue to be housed within tongue sleeve 703. Alternatively, several sizes may be offered for tongue sleeve 703, whereby a more severe manifestation of snoring or sleep apnea is accompanied by a respective increase in the amount of anterior tongue matter allowably housed in tongue sleeve 703.

Figure 12C:
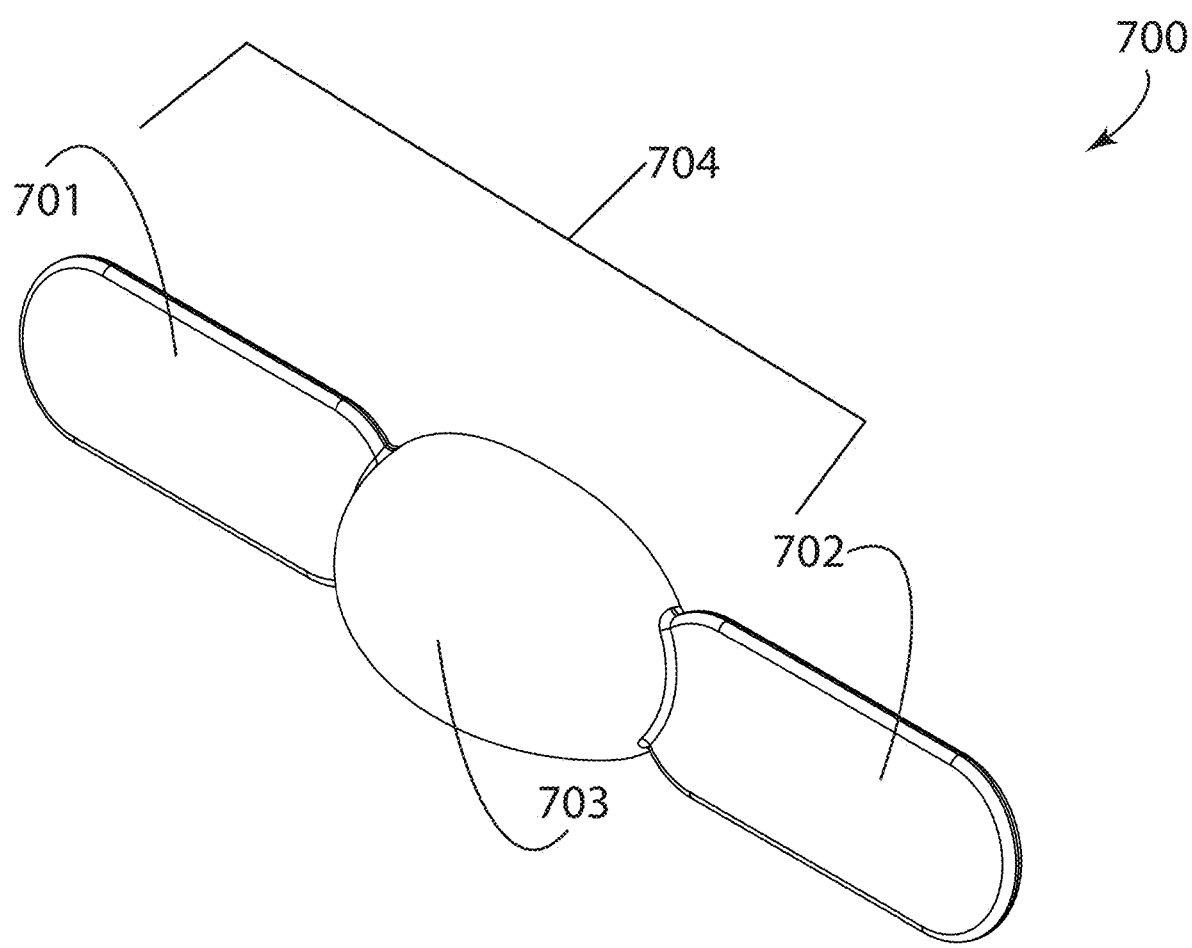
FIG. 12(c) is a perspective view of one embodiment of a dental appliance in accordance with the present invention.

Turning now to the next figure, FIG. 12(c) illustrates a perspective view of a dental appliance in accordance with one embodiment of the present invention. As may be appreciated by this figure, first arm 701 and second arm 702 of mouthpiece 704 may be completely smooth and devoid of openings or protrusions. Of course, it is also envisioned by the present invention that first arm 701 and second arm 702 may be textured, perforated, or decorated. These and other styles known in the art are contemplated by the present invention.

In some embodiments of the present invention, first arm 701 and second arm 702 may be comprised of ends that are arched. Having the ends of first arm 701 and second arm 702 arched may allow a user to more easily store dental appliance 700. Of course, first arm 701 and second arm 702 may have ends that are other shapes without deviating from the scope or spirit of the present invention. By way of example and not limitation, the ends of first arm 701 and second arm 702 may be rectangular, triangular, or any other shape known in the art.

In some embodiments, first arm 701 and second arm 702 may be attached to tongue sleeve 703 along a horizontal axis of tongue sleeve 703 and equidistant from a central axis point of tongue sleeve 703.

Figure 12D:
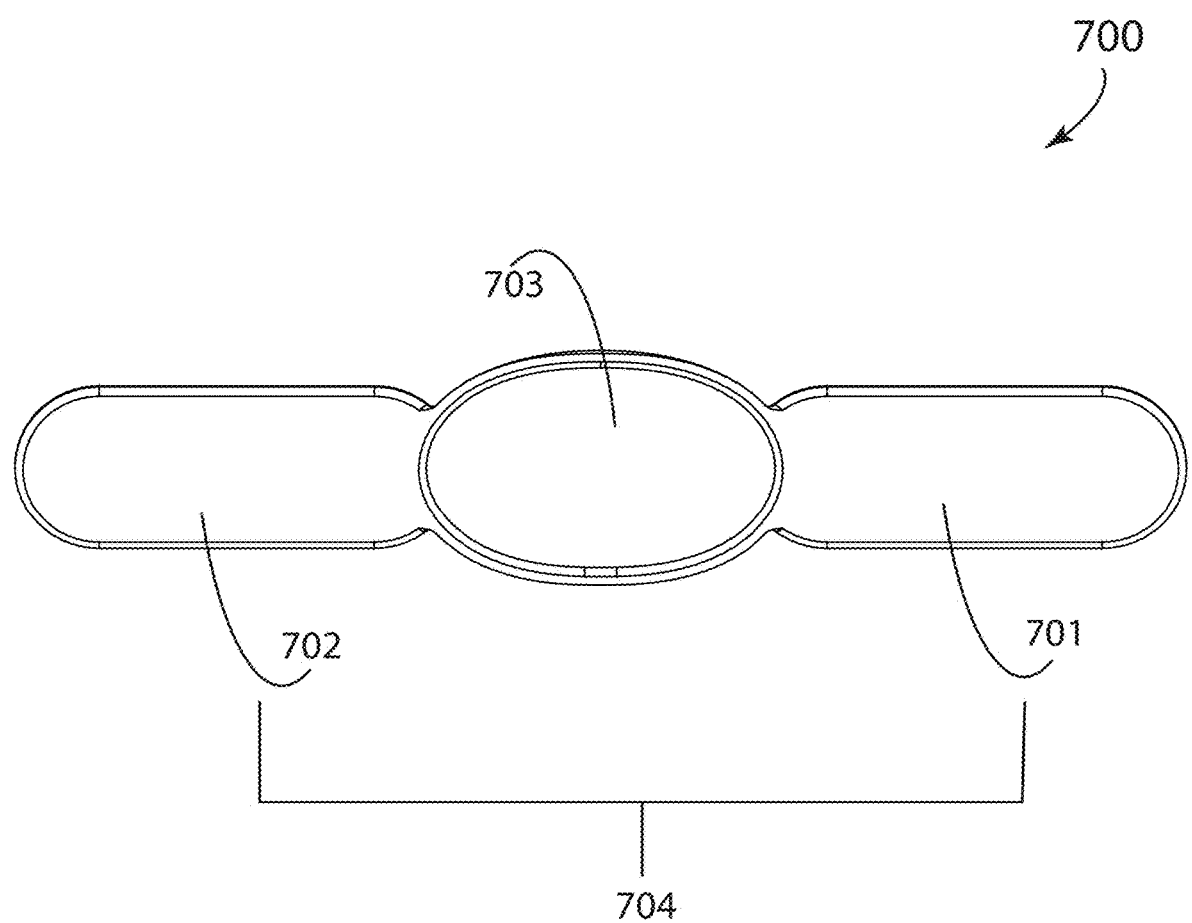
FIG. 12(d) is a back view of one embodiment of a dental appliance in accordance with the present invention.

FIG. 12(d) is a back view of the tongue sleeve. In an exemplary embodiment, tongue sleeve 703, in accordance with the present invention, may utilize a light suction to adjoin the tongue to the interior of tongue sleeve 703. In an exemplary embodiment, air may first be expelled from tongue sleeve 703 by squeezing tongue sleeve 703—the vacuum created by the expelled air may aid in snugly fitting the tongue thereafter. To reverse the process and remove the tongue from tongue sleeve 703, the user may again squeeze tongue sleeve 703.

In another embodiment, tongue sleeve 703 may instead utilize a gentle clamp which allows for interaction with mouthpiece 704 to secure the tongue in a configuration further forward than a tongue may typically rest.

Figure 13A:
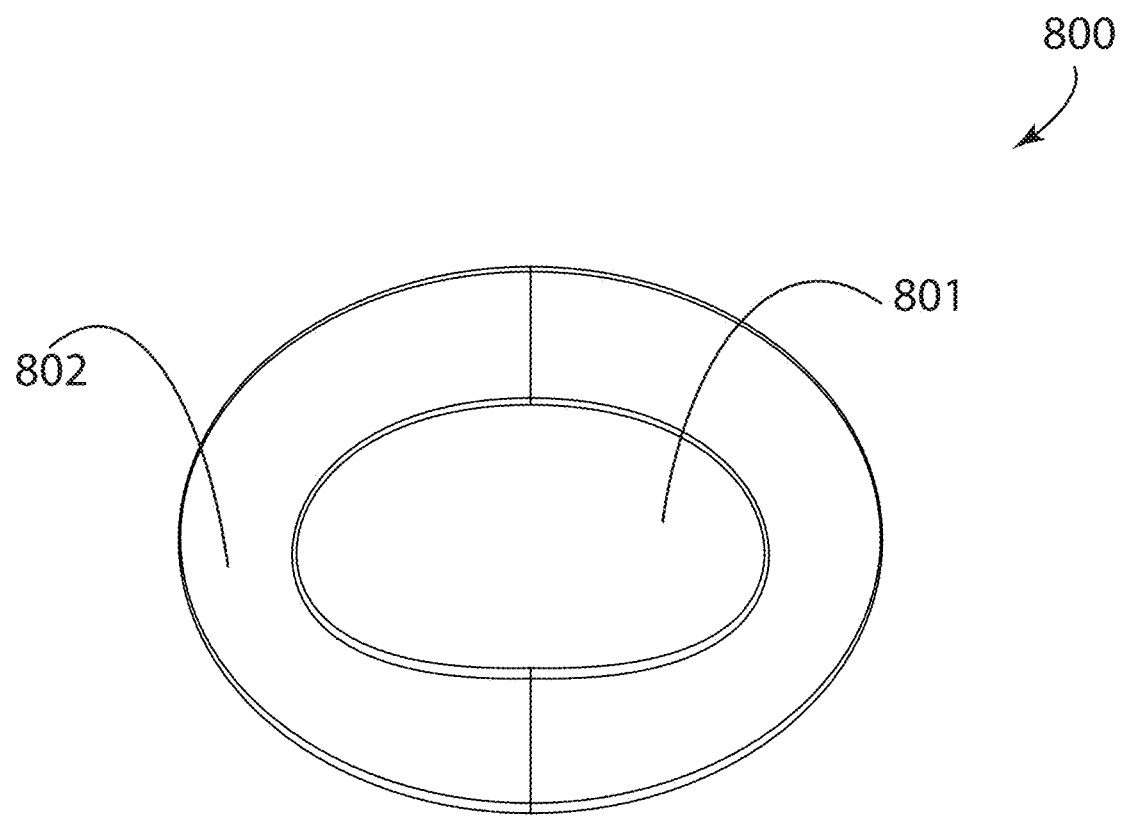
FIG. 13(a) is a front view of one embodiment of a dental appliance in accordance with the present invention.

Turning now to the next figure, FIG. 13(a) is a front view of a dental appliance in accordance with one embodiment of the present invention. Specifically, FIG. 13(a) illustrates dental appliance 800, which includes tongue sleeve 801, exterior surface 802, and interior surface 803. Dental appliance 800, of which a plurality of embodiments is disclosed herein, produces no audible sound since it does not require a machine or motor, and as such, does not impede restful sleep for the user or those nearby. Moreover, dental appliance 800 includes tongue sleeve 801 which uniquely functions to keep the user's tongue in a position that allows for an airway to remain open.

It is envisioned that dental appliance 800 may rest on top of and extend outwardly from a user's mouth when the user's tongue is inserted into tongue sleeve 801, similar to a reverse pacifier. By way of example and not limitation, a user may secure their tongue within tongue sleeve 801 and secure dental appliance 800 by placing their tongue within a concaved cavity of tongue sleeve 301. The concaved cavity of tongue sleeve 801 may have an interior concaved surface devoid of openings.

The material from which dental appliance 800 may be constructed is not to be limited. For example, and without limitation, dental appliance 800 may be comprised of a number of types of polymers, copolymers, or plastics, such as thermoplastics, as well as harder materials such as gold or acrylic, or alloys composed of such materials as cobalt or chrome. Alternatives to the enumerated materials should be apparent to those skilled in the art.

Tongue sleeve 801 receives a user's tongue and securely holds the tongue in a forward configuration relative to the user's mouth. Tongue sleeve 801 serves as a tongue-receiving member. Tongue sleeve 801 may comprise multiple components or a single component without deviating from the scope of the present invention. For example, tongue sleeve 801 may be a clamping device, a suction device, or any general retaining device. In one embodiment, tongue sleeve 801 comprises a flexible, substantially spherical or semi-spherical protrusion including an inner surface comprising a concaved portion suitable for receiving a tip portion of the user's tongue. In such an embodiment, tongue sleeve 801 may implement suction to keep the tongue securely within tongue sleeve 801.

Figure 13B:
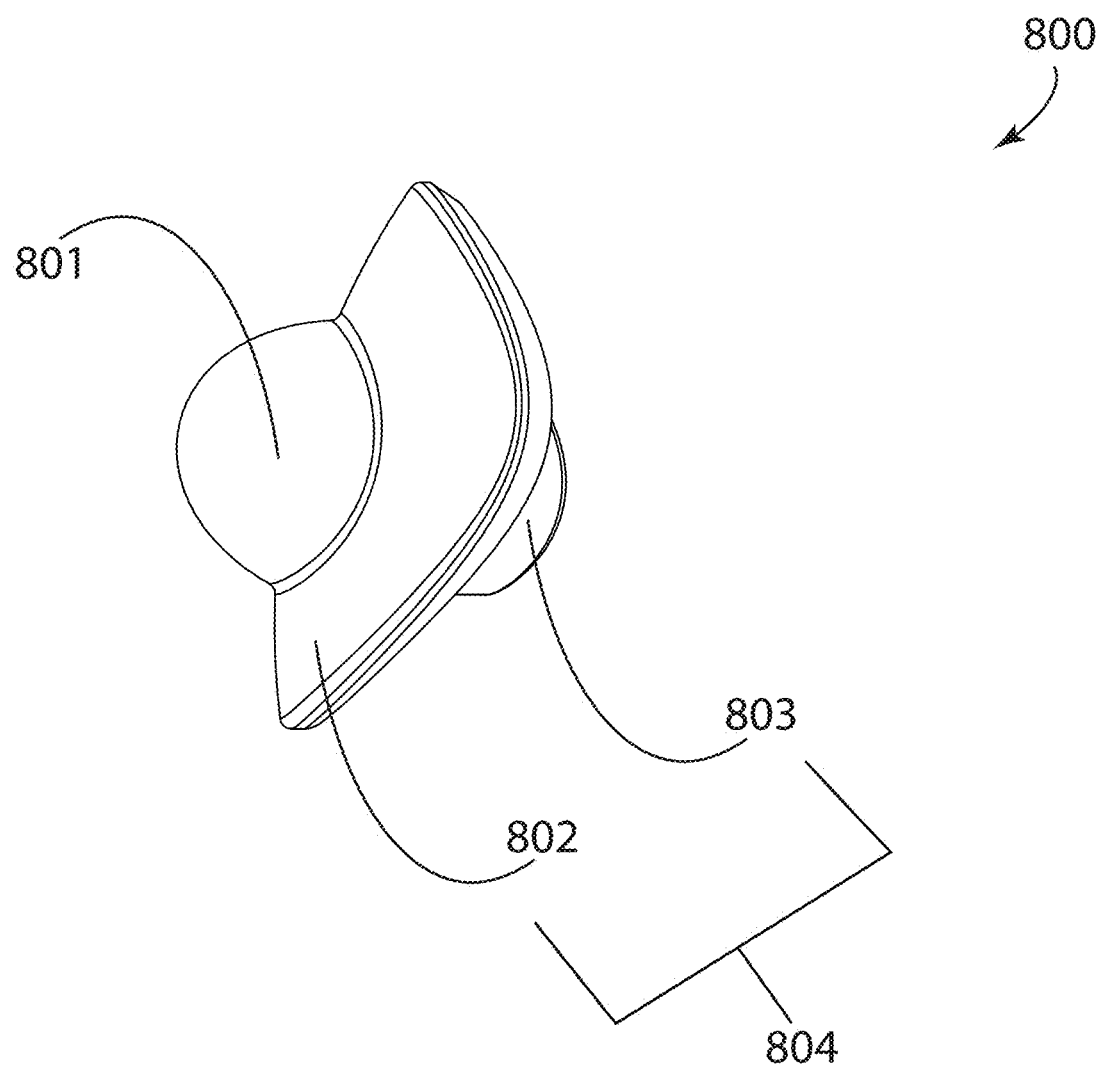
FIG. 13(b) is a side view of one embodiment of a dental appliance in accordance with the present invention, showing the left side of the device.

FIG. 13(b) is a side view of a dental appliance in accordance with one embodiment of the present invention. As may be better illustrated by this figure, exterior surface 802 and interior surface 803 make up what may be referred to as mouthpiece 804. Tongue sleeve 801 may be integral with mouthpiece 804. Of course, it is also envisioned that tongue sleeve 801 may be removably attached to mouthpiece 804. This feature (i.e., a removable tongue sleeve 801) may be desirable for use during times in which the user determines his or her snoring and sleep apnea are less severe. Conversely, if a user typically has little cause for concern of the tongue receding and thereby impeding respiration, but by a change in circumstance the need for tongue sleeve 801 arises, such a user may attach and detach tongue sleeve 801 accordingly.

In some embodiments of the present invention, tongue sleeve 801 may be secured to mouthpiece 804 by utilizing an adhesive material, such as but not limited to: epoxy, sealant, hot melt, or any other suitable adhesive. Such adhesives may be used to permanently or removably affix tongue sleeve 801 to mouthpiece 804.

Still other embodiments may employ different methods for securing tongue sleeve 801 to mouthpiece 804. For example, tongue sleeve 801 may be removably affixed to mouthpiece 804 using a simple locking mechanism such as a mechanism that may snap, slide, or click into place upon proper insertion of tongue sleeve 801 into mouthpiece 804.

Tongue sleeve 801 may be located at an intersection point between a horizontal axis and a vertical axis of mouthpiece 804 such that mouthpiece circumscribes tongue sleeve 801.

In various embodiments, tongue sleeve 801 may be malleable insofar as it provides sufficient internal flexibility for comfortable securement of the user's tongue, but not so malleable as to enable the user to drastically alter the shape of tongue sleeve 801 whereby any efficacy of dental appliance 800 is lost.

As may be better appreciated by this figure, exterior surface 802 and interior surface 803 of mouthpiece 804 may be completely smooth and devoid of openings or protrusions (save for where tongue sleeve 801 may connect to mouthpiece 804). However, exterior surface 802 and interior surface 803 may be comprised of a plurality of perforations without deviating from the spirit and scope of the present invention. Such perforations may allow a user to increase their oxygen intake while using the dental appliance 800.

In accordance with some embodiments of the present invention, a user may operate dental appliance 800 by inserting the user's tongue into tongue sleeve 801. After insertion of the tongue, mouthpiece 804 may rest over the user's mouth with interior surface 803 adjacent to the user's mouth and face.

Figure 13C:
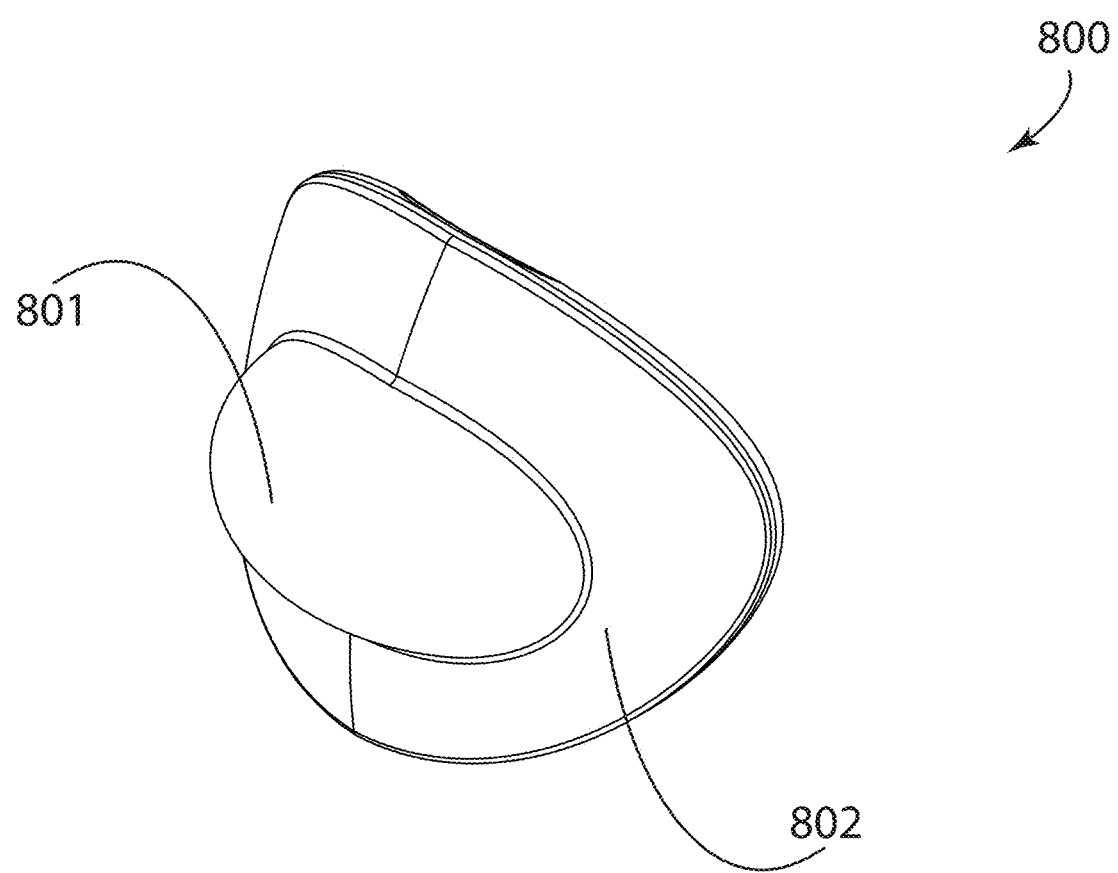
FIG. 13(c) is a perspective view of one embodiment of a dental appliance in accordance with the present invention, showing the left side of the device.

Turning now to the next figure, FIG. 13(c) illustrates a perspective view of a dental appliance in accordance with one embodiment of the present invention. Typically, the tongue approaches tongue sleeve 801, reserving only enough space for the tip of the tongue to enter. In one embodiment, tongue sleeve 801 may come in a plurality of sizes. In exemplary embodiments, tongue sleeve 801 extends beyond exterior surface 802 by as little as 1 or 2 millimeters or as much as 2 centimeters, similarly allowing as little as 1 or 2 millimeters or as much as 2 centimeters of the anterior segment of the tongue to be housed within tongue sleeve 301. Alternatively, several sizes may be offered for tongue sleeve 801, whereby a more severe manifestation of snoring or sleep apnea is accompanied by a respective increase in the amount of anterior tongue matter allowably housed in tongue sleeve 801.

As may also be seen by FIGS. 13(b) and 13(c), exterior surface 802 and interior surface 803 may be formed in such a way that mouthpiece 804 may have a parabolic shape. Forming mouthpiece 804 in this manner may allow the dental appliance 800 to more easily stay on a user's face. Of course, exterior surface 802 and interior surface 803 may be formed in other ways such that mouthpiece 804 is a shape other than parabola. For example, mouthpiece 804 may be flat. This and other shapes known in the art may be implemented without deviating from the scope and spirit of the present invention.

Figure 13D:
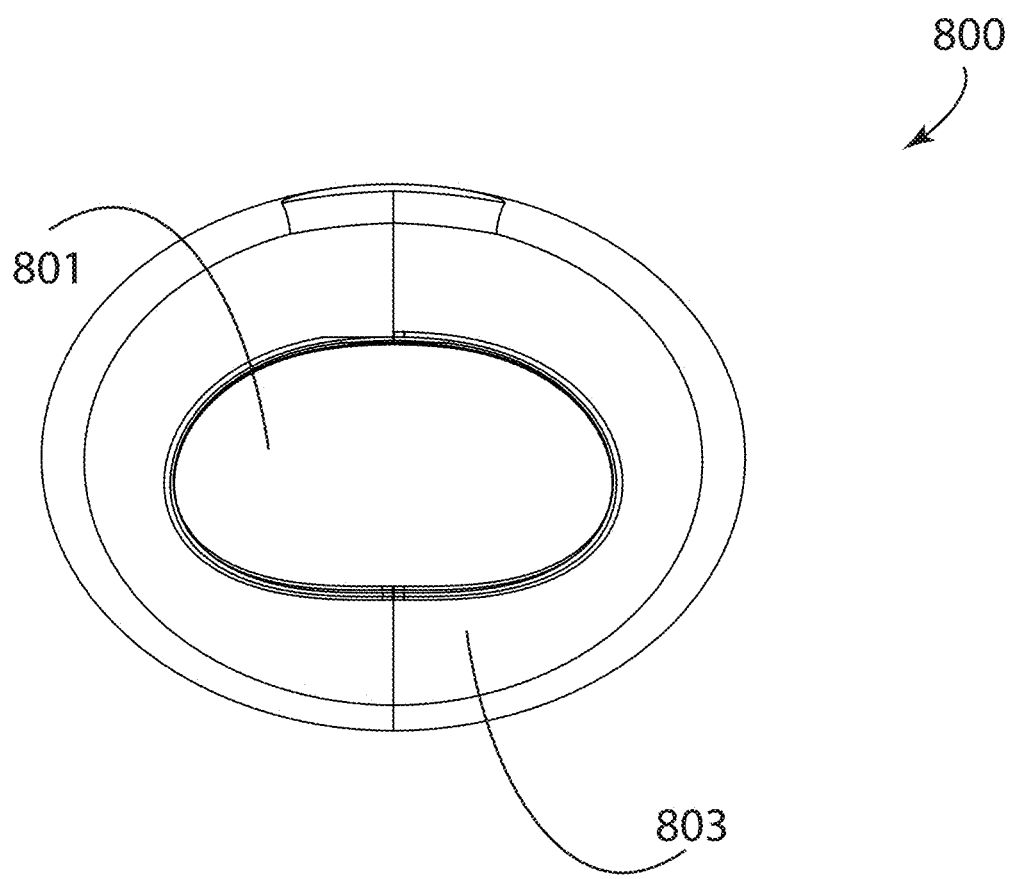
FIG. 13(d) is a back view of one embodiment of a dental appliance in accordance with the present invention.

FIG. 13(d) is a back view of the dental appliance. In an exemplary embodiment, tongue sleeve 801, in accordance with the present invention, may utilize a light suction to adjoin the tongue to the interior of tongue sleeve 801. In an exemplary embodiment, air may first be expelled from tongue sleeve 801 by squeezing tongue sleeve 801—the vacuum created by the expelled air may aid in snugly fitting the tongue thereafter. To reverse the process and remove the tongue from tongue sleeve 801, the user may again squeeze tongue sleeve 801.

In another embodiment, tongue sleeve 801 may instead utilize a gentle clamp which allows for interaction with mouthpiece 804 to secure the tongue in a configuration further forward than a tongue may typically rest.

A dental appliance, including a mouthpiece equipped with a tongue-retaining mechanism, has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A dental appliance for alleviating snoring and other sleep disorders, comprising:
   a mouthpiece including two substantially semicircular components together forming a base with a surface adapted to fit it inside a user's mouth within the confines of the user's upper and lower lips, wherein the surface of the mouthpiece is defined by an exterior surface adapted to contact an interior of the user's upper and lower lips and an interior surface adapted to contact the user's dental arch;
   a tongue sleeve attached to the mouthpiece, the tongue sleeve including a semi-spherical component comprising a concaved cavity having an interior concaved surface devoid of openings; and
   at least one opening formed by a spatial gap between the mouthpiece and the tongue sleeve, the two substantially semicircular components of the mouthpiece in a separated position, the at least one opening adapted to allow airflow through the user's mouth.

2. The dental appliance of claim 1, wherein the tongue sleeve is integral with the mouthpiece.

3. The dental appliance of claim 1, wherein the tongue sleeve protrudes forward from an anterior end of the mouthpiece.

4. The dental appliance of claim 1, wherein the exterior surface and the interior surface are completely smooth.

5. The dental appliance of claim 1, wherein the tongue sleeve utilizes a light suction to adjoin the tongue to the tongue sleeve.

6. The dental appliance of claim 1, wherein the tongue sleeve utilizes a gentle clamp to adjoin the tongue to the tongue sleeve.

7. The dental appliance of claim 1, wherein the mouthpiece is curved to fit inside the user's mouth.

8. A dental appliance for alleviating snoring and other sleep disorders, comprising:
   a mouthpiece including two substantially semicircular components together forming a base with a surface adapted to fit it inside a user's mouth within the confines of the user's upper and lower lips, wherein the surface of the mouthpiece is defined by an exterior surface adapted to contact an interior of the user's upper and lower lips and an interior surface adapted to contact the user's dental arch;
   a tongue sleeve situated between a maxillary region and a mandibular region of the surface of the mouthpiece, wherein:
   the tongue sleeve includes a semi-spherical portion, comprising a concaved cavity including an interior concaved surface devoid of openings for securely receiving a tip portion of the user's tongue; and
   at least one opening formed by a spatial gap between the mouthpiece and the tongue sleeve, the two substantially semicircular components of the mouthpiece in a separated position, the at least one opening adapted to allow airflow through the user's mouth.

9. The dental appliance of claim 8, wherein the tongue sleeve is integral with the mouthpiece.

10. The dental appliance of claim 8, wherein the tongue sleeve protrudes forward from an anterior end of the mouthpiece.

11. The dental appliance of claim 8, wherein the surface of the mouthpiece is completely smooth.

12. The dental appliance of claim 8, wherein the tongue sleeve utilizes a light suction to adjoin the tongue to the tongue sleeve.

13. The dental appliance of claim 8, wherein the tongue sleeve utilizes a gentle clamp to adjoin the tongue to the tongue sleeve.

14. A dental appliance for alleviating snoring and other sleep disorders, comprising:
   a mouthpiece comprising two substantially semicircular components together forming a base with a region adapted to fit it inside a user's mouth within the confines of the user's upper and lower lips, the region of the mouthpiece including a completely smooth exterior surface and a completely smooth interior surface, wherein the region of the mouthpiece is defined by an exterior surface adapted to contact an interior of the user's upper and lower lips and an interior surface adapted to contact the user's dental arch;
   a tongue sleeve situated between the exterior surface and the interior surface, wherein:
   the tongue sleeve includes a semi-spherical portion, comprising a concaved cavity including an interior concaved surface devoid of openings adapted to securely receive a tip portion of the user's tongue; and
   at least one opening formed by a spatial gap between the mouthpiece and the tongue sleeve, the two substantially semicircular components of the mouthpiece in a separated position, the at least one opening adapted to allow airflow through the user's mouth.

15. The dental appliance of claim 14, wherein the tongue sleeve is integral with the mouthpiece.

16. The dental appliance of claim 14, wherein the tongue sleeve protrudes forward from an anterior end of the mouthpiece.

17. The dental appliance of claim 14, wherein the tongue sleeve utilizes a light suction to adjoin the tongue to the tongue sleeve.

18. The dental appliance of claim 14, wherein the tongue sleeve utilizes a gentle clamp to adjoin the tongue to the tongue sleeve.

* * * * *